(12) United States Patent
Patil et al.

(10) Patent No.: US 12,258,448 B2
(45) Date of Patent: Mar. 25, 2025

(54) METHOD OF MAKING A BIPHENOL DIANHYDRIDE COMPOSITION, METHOD FOR PURIFICATION OF A BIPHENOL DIANHYDRIDE COMPOSITION, AND POLY (ETHERIMIDES) DERIVED FROM THE BIPHENOL DIANHYDRIDE

(71) Applicant: SHPP GLOBAL TECHNOLOGIES B.V., Bergen op Zoom (NL)

(72) Inventors: Dadasaheb V. Patil, Mt. Vernon, IN (US); James Patrick Schulte, II, Mt. Vernon, IN (US)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 770 days.

(21) Appl. No.: 17/417,525

(22) PCT Filed: Jan. 29, 2020

(86) PCT No.: PCT/US2020/015657
§ 371 (c)(1),
(2) Date: Jun. 23, 2021

(87) PCT Pub. No.: WO2020/160132
PCT Pub. Date: Aug. 6, 2020

(65) Prior Publication Data
US 2022/0162386 A1 May 26, 2022

(30) Foreign Application Priority Data
Jan. 31, 2019 (EP) ..................................... 19154907

(51) Int. Cl.
*C07D 307/89* (2006.01)
*C08G 73/10* (2006.01)

(52) U.S. Cl.
CPC ....... *C08G 73/1071* (2013.01); *C07D 307/89* (2013.01); *C08G 73/1032* (2013.01); *C08G 73/1053* (2013.01)

(58) Field of Classification Search
CPC ............ C08G 73/1071; C08G 73/1032; C08G 73/1053; C08G 73/1064; C08G 73/1046; C07D 307/89
USPC ........................................................ 549/250
See application file for complete search history.

(56) References Cited

U.S. PATENT DOCUMENTS

| | | |
|---|---|---|
| 3,879,428 A | 4/1975 | Heath et al. |
| 3,905,942 A | 9/1975 | Takekoshi et al. |
| 3,956,320 A | 5/1976 | Heath et al. |
| 4,293,683 A | 10/1981 | Takekoshi et al. |
| 4,324,882 A | 4/1982 | Takekoshi |
| 4,623,732 A | 11/1986 | Peters |
| 4,808,731 A | 2/1989 | Berdahl et al. |
| 4,906,760 A * | 3/1990 | Mueller ................ C07C 51/573 549/241 |
| 6,727,370 B1 | 4/2004 | Brunelle et al. |
| 7,495,113 B2 | 2/2009 | Pressman et al. |
| 2006/0066004 A1 | 3/2006 | Richards et al. |
| 2006/0135791 A1* | 6/2006 | Pressman ................ C07C 51/47 549/281 |
| 2006/0205958 A1 | 9/2006 | Brunelle et al. |
| 2006/0293528 A1 | 12/2006 | Stella et al. |
| 2007/0073035 A1 | 3/2007 | Stella et al. |
| 2007/0073066 A1 | 3/2007 | Stella et al. |

FOREIGN PATENT DOCUMENTS

| | | |
|---|---|---|
| CN | 101402625 A | 4/2009 |
| CN | 101696199 B | 9/2011 |
| CN | 106279085 A | 1/2017 |
| EP | 0401606 A1 | 12/1990 |
| EP | 593200 | 4/1994 |
| EP | 1674443 A1 | 6/2006 |
| JP | S6299371 A | 5/1987 |
| WO | 2017132656 A1 | 8/2017 |
| WO | 2017172593 A1 | 10/2017 |

OTHER PUBLICATIONS

International Search Report for the corresponding International Application No. PCT/US2020/015657; International Filing Date: Jan. 29, 2020; Date of Mailing: May 4, 2020; 6 pages.
Takekoshi, T. et al., "Polyetherimides. I. Preparation of Dianhydrides Containing Aromatic Ether Groups", Journal of Polymer Science: Polymer Chemistry Edition, vol. 23, 1985; pp. 1759-1769.
Takekoshi, T. et al., "Polyetherimides. II. High-Temperature Solution Polymerization", Journal of Polymer Science: Polymer Symposium, vol. 74, 1986; pp. 93-108.
Written Opinion for the corresponding International Application No. PCT/US2020/015657; International Filing Date: Jan. 29, 2020; Date of Mailing: May 4, 2020; 9 pages.

* cited by examiner

*Primary Examiner* — Taylor V Oh
(74) *Attorney, Agent, or Firm* — CANTOR COLBURN LLP

(57) ABSTRACT

A method for purification of a biphenol dianhydride composition includes contacting the biphenol dianhydride composition with a halogenated solvent to form a solution, and isolating the purified biphenol dianhydride composition from the solution. A method of making a biphenol dianhydride composition including contacting a first solution including a biphenol tetraacid, and at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions, with a halogenated solvent to provide a second solution, heating the second solution to form the corresponding biphenol dianhydride, and isolating the purified biphenol dianhydride. The biphenol dianhydride is particularly useful for forming poly(etherimides), which can be used in a variety of articles.

10 Claims, No Drawings

METHOD OF MAKING A BIPHENOL DIANHYDRIDE COMPOSITION, METHOD FOR PURIFICATION OF A BIPHENOL DIANHYDRIDE COMPOSITION, AND POLY(ETHERIMIDES) DERIVED FROM THE BIPHENOL DIANHYDRIDE

CROSS-REFERENCE TO RELATED APPLICATIONS

This application is a National Stage application of PCT/US2020/015657, filed Jan. 29, 2020, which claims the benefit of European patent application number 19154907.0 filed on Jan. 31, 2019, both of which are hereby incorporated by reference in their entirety.

BACKGROUND

Poly(imides), and in particular, poly(etherimides) (PEI), are high performance polymers having a glass transition temperature (Tg) of greater 180° C. These polymers further have high strength, heat resistance, and modulus, and broad chemical resistance. Poly(etherimides) are widely used in applications as diverse as automotive and electrical/electronic applications since these compositions offer good mechanical and thermal properties.

Poly(etherimides) can be prepared by condensation polymerization, for example of a dianhydride with a diamine. In order to obtain good reaction kinetics, achieve high molecular weight, and provide a stable, processable polymer product, high purity monomer components are desirable. Additionally, some applications can require that the polymers have good optical clarity, and good thermal and mechanical properties. The level of haze exhibited by an article can be related to the method by which the polymer is prepared. In practice, it can be difficult to produce the desired dianhydrides that are substantially free of metals and their salts.

Therefore, there is a need in the art for dianhydride monomers that are substantially free of residual phase transfer agents, sodium, potassium, calcium, zinc, aluminum, iron, nickel, titanium, phosphorus, chromium, magnesium, manganese, copper, phosphate, nitrate, nitrite, sulfate, bromide, fluoride, and chloride ions. It would be a further advantage to provide poly(etherimides) that have low levels of such contaminants, and exhibit low haze, high optical clarity, good reaction kinetics during polymerization, high molecular weight, and behave as stable and processable polymers.

SUMMARY

A method for the purification of a biphenol dianhydride composition comprising a biphenol dianhydride of the formula

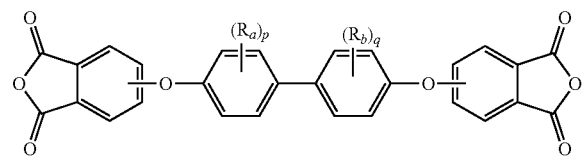

wherein $R^a$ and $R^b$ are each independently a halogen or a monovalent $C_{1-6}$ alkyl group and p and q are each independently an integer of 0 to 4, preferably wherein p and q are each 0; and at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions; wherein the method comprises contacting the biphenol dianhydride composition with a halogenated solvent under conditions effective to form a solution comprising the biphenol dianhydride composition; and isolating a purified biphenol dianhydride composition from the solution wherein isolating the purified biphenol dianhydride composition from the solution comprises: cooling the solution to induce crystallization of the purified biphenol dianhydride composition to form a slurry, filtering the slurry to form a wet cake comprising the purified biphenol dianhydride composition, and washing the wet cake with water, a $C_{1-6}$ alcohol, or a combination thereof; filtering the solution, preferably wherein the filtering is at a temperature of 160 to 225° C., preferably 160 to 190° C., more preferably 165 to 185° C., and optionally cooling the filtered solution to crystallize the purified biphenol dianhydride composition; washing the solution with an aqueous alkaline solution, preferably wherein the aqueous alkaline solution comprises sodium bicarbonate; or adding an adsorbent to the solution to remove ionic species from the solution, and filtering the solution to remove the adsorbent and ionic species; or a combination thereof.

A method of making a biphenol dianhydride composition comprises contacting a first solution comprising a biphenol tetraacid of the formula

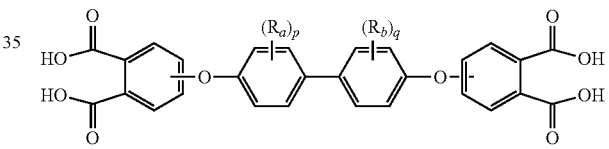

wherein $R^a$ and $R^b$ are each independently a halogen or a monovalent $C_{1-6}$ alkyl group and p and q are each independently an integer of 0 to 4, preferably wherein p and q are each 0; and at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions; with a halogenated solvent to provide a second solution; subjecting the second solution to a condition effective to form the corresponding biphenol dianhydride from the biphenol tetraacid; and isolating a purified biphenol dianhydride composition, wherein isolating the purified biphenol dianhydride composition from the solution comprises: cooling the solution to induce crystallization of the purified biphenol dianhydride composition to form a slurry, filtering the slurry to form a wet cake comprising the purified biphenol dianhydride composition, and washing the wet cake with water, a $C_{1-6}$ alcohol, or a combination thereof; filtering the solution, preferably wherein the filtering is at a temperature of 160 to 225° C., preferably 160 to 190° C., more preferably 165 to 185° C., and optionally cooling the filtered solution to crystallize the purified biphenol dianhydride composition; or adding an adsorbent to the solution to remove ionic species from the solution, and filtering the solution to remove the adsorbent and ionic species; or a combination thereof.

A biphenol dianhydride made by the method above, wherein the purified biphenol dianhydride comprises less than 25 ppm each of sodium ions, potassium ions, calcium ions, zinc ions, aluminum ions, nickel ions, titanium ions, chromium ions, magnesium ions, manganese ions, copper ions iron ions, phosphorus ions; less than 175 ppm total of sodium ions, potassium ions, calcium ions, zinc ions, aluminum ions, nickel ions, titanium ions, chromium ions, magnesium ions, manganese ions, copper ions, iron ions and phosphorus ions; less than 35 ppm each of phosphate ions, sulfate ions, chloride ions, bromide ions, fluoride ions, nitrate ions, and nitrite ions; and less than 50 ppm total of phosphate ions, sulfate ions, chloride ions, bromide ions, fluoride ions, nitrate ions, and nitrite ions.

A poly(etherimide) comprising repeating units derived from polymerization of the purified biphenol dianhydride composition and one or more organic diamine represents another aspect of the present disclosure.

An article comprises the poly(etherimide), preferably wherein the article is an optical component.

The above described and other features are exemplified by the following detailed description.

DETAILED DESCRIPTION

The present inventors have unexpectedly discovered that biphenol dianhydrides can be prepared having low levels of residual contaminants, in particular through the use of a halogenated solvent. The present inventors have also discovered a method for preparing the biphenol dianhydride from the corresponding tetraacid precursor using a halogenated solvent. Advantageously, the biphenol dianhydride can be used for polymerization with a diamine to provide poly(etherimides) having low levels of residual contaminants, affording the polymers with desired properties, in particular, good optical clarity and low haze. The poly(etherimides) having a rigid backbone based on a biphenol moiety were found to achieve high molecular weight when prepared using a halogenated solvent.

Accordingly, an aspect of the present disclosure is a method of making a biphenol dianhydride from the corresponding biphenol tetraacid precursor. The method comprises contacting a biphenol tetraacid, and at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions with a halogenated solvent to provide a first solution. The biphenol tetraacid is of the formula

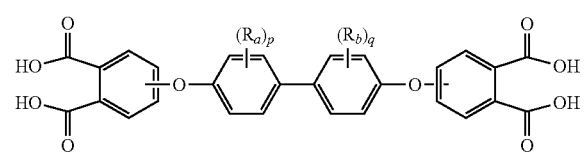

wherein $R^a$ and $R^b$ are each independently a halogen or a monovalent $C_{1-6}$ alkyl group and p and q are each independently an integer of 0 to 4, preferably wherein p and q are each 0. In some embodiments, p, q, or both can be 1 to 4, preferably 1 to 2, more preferably 1. In some embodiments, $R^a$ and $R^b$ can each independently be a $C_{1-3}$ alkyl group, for example a methyl group. The divalent bonds of the biphenol group can be in the 3,3' position, the 3,4' position, 4,3'- or the 4,4' position. Preferably, the divalent bonds of the biphenol group can be in the 3,3' position. The biphenol tetraacid can be prepared from hydrolysis of an aromatic bisimide precursor, for example as further described in the working examples below. The biphenol tetraacid preferably comprises less than 0.5 weight percent of a biphenol contaminant. In some embodiments, the biphenol tetraacid preferably comprises 200 ppm or less of sodium ions.

The halogenated solvent is preferably an aromatic halogenated solvent. For example, illustrative halogenated solvents can include ortho-dichlorobenzene, meta-dichlorobenzene, para-dichlorobenzene, 1,3,5-trichlorobenzene, 1,2,3-trichlorobenzene, 1,2,4-trichlorobenzene, 1,2,4,5-tetrachlorobenzene, 1,2,3,4-tetrachlorobenzene, 1,2,3,5-tetrachlorobenzene, chlorobenzene, bromobenzene, 2-chlorophenol, 4-chlorophenyl phenyl ether, m-chlorotoluene, o-chlorotoluene, p-chlorotoluene, and the like, or a combination thereof. In an embodiment, the halogenated solvent can be ortho-dichlorobenzene. In some embodiments, other solvents can be excluded from the present method. For example, the method can exclude a non-halogenated solvent, in particular, a non-halogenated aromatic solvent.

The first solution is heated under conditions effective to provide a second solution comprising the corresponding biphenol dianhydride. The biphenol dianhydride can be of the formula

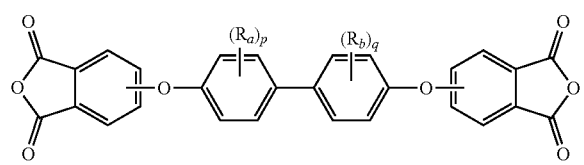

wherein $R^a$, $R^b$, p and q are as defined above. In a specific embodiment, p and q are zero, and the divalent bonds of the biphenol group are in the 3,3' position. In some embodiments, the biphenol dianhydride can be an isomer mixture. For example, 2-100 weight percent of the biphenol dianhydride can have the divalent bonds of the biphenol group of the biphenol dianhydride in the 3,3' position. Preferably, 90-100 weight percent of the biphenol dianhydride can have the divalent bonds of the biphenol group of the biphenol dianhydride in the 3,3' position. Thus, the biphenol dianhydride preferably is an isomer mixture wherein 90 to 100 weight percent of the biphenol dianhydride has the formula

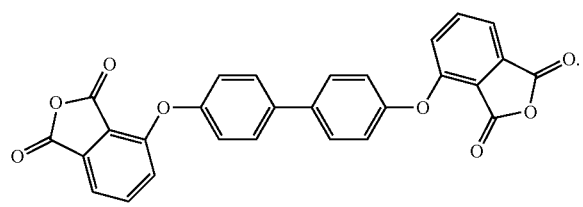 [SMILES: O=C1OC(=O)c2c(Oc3ccc(-c4ccc(Oc5cccc6c5C(=O)OC6=O)cc4)cc3)cccc21]

The second solution can further comprise the at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions, and the halogenated solvent The conditions effective to provide the second solution can include, for example, a temperature of 100 to 250° C., preferably 150 to 200° C., more preferably 175 to 195° C. and a time of 5 minutes to 10 hours, preferably 1 to 10 hours, more preferably 1 to 5 hours. The heating can be conducted under high pressure, at reduced pressure, or at atmospheric pressure. In some embodiments, the method is preferably conducted in the absence of dehydrating agents such as acetic acid, acetic anhydride, and the like, or a combination thereof. In some embodiments, phase transfer catalysts are excluded from the method.

The method further comprises isolating the purified biphenol dianhydride. Isolating can be by, for example, filtration, centrifugation, and the like, or a combination thereof. In some embodiments, the second solution can be cooled prior to isolation, for example to a temperature of less than 200° C., or less than 180° C., preferably less than 150, more preferably less than 100° C. to induce crystallization of the purified biphenol dianhydride to form a slurry. In some embodiments, the method comprises isolating the crystallized purified biphenol dianhydride by filtration to form a wet cake, and optionally washing the wet cake with water, a $C_{1-6}$ alcohol, or a combination thereof, preferably methanol, water, or a combination thereof, more preferably water. In some embodiments, the method comprises contacting the second solution with an aqueous alkaline solution to a temperature of less than 100° C., or less than 90° C., preferably 50-85° C. for a sufficient time, phase separating the mixture, isolating the purified biphenol dianhydride by filtration to form a wet cake, and optionally washing the wet cake with water, a $C_{1-61}$ alcohol, or a combination thereof, preferably methanol, water, or a combination thereof, more preferably water. The aqueous alkaline solution can have a pH less than 14, preferably less than 10, more preferably 7.5 to 8.5. It is also noted that contacting the solution with the aqueous alkaline solution at the temperatures indicated can induce crystallization of the biphenol dianhydride, and thus the resulting slurry can be washed with the aqueous alkaline solution.

Prior to isolation, the solution can have a solids content of 2 to 25 weight percent, preferably 5 to 25, more preferably 7 to 15 weight percent. In some embodiments, the solution can be filtered, for example at a temperature of 225 to 250° C., preferably 220-225° C., more preferably 180-200, even more preferably 160 to 185° C., which can remove insoluble organic and inorganic salts. After filtration, the purified biphenol dianhydride can be used directly (e.g., for polymerization), or can be crystallized by cooling the solution, followed by filtration to isolate the purified biphenol dianhydride.

Another aspect of the present disclosure is a method for the purification of a biphenol dianhydride composition. The biphenol dianhydride composition comprises a biphenol dianhydride of the above formula, and at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions. The method comprises contacting the biphenol dianhydride composition with a halogenated solvent to form a solution comprising the biphenol dianhydride composition, and isolating the biphenol dianhydride composition. After contacting the biphenol dianhydride composition with the halogenated solvent and isolating the biphenol dianhydride composition, the isolated biphenol dianhydride composition comprises a reduced concentration of the at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions, for example various inorganic salts including $NaHSO_3$, $Na_2SO_4$, $KHSO_3$, $K_2SO_4$, $NaNO_3$, $NaNO_2$, $KNO_3$, $KNO_2$, NaCl, KCl, $CaSO_4$, and $Ca(NO_3)_2$.

Isolating the biphenol dianhydride composition can be by, for example, filtration, centrifugation, and the like, or a combination thereof. In an embodiment, isolating the purified biphenol dianhydride composition comprises cooling the solution to induce crystallization of the purified biphenol dianhydride composition to form a slurry, filtering the slurry to form a wet cake comprising the purified biphenol dianhydride composition, and the method further comprises washing the wet cake with water, a $C_{1-6}$ alcohol, or a combination thereof.

In some embodiment, isolating the purified biphenol dianhydride composition comprises filtering the solution, preferably wherein the filtering is at a temperature of 160 to 225° C., preferably 160 to 190° C., more preferably 165 to 185° C., and optionally cooling the filtered solution to crystallize the purified biphenol dianhydride composition. Filtering at elevated temperature can remove insoluble inorganic salts.

In some embodiments, isolating the purified biphenol dianhydride composition comprises washing the solution with an aqueous alkaline solution, preferably wherein the aqueous alkaline solution comprises sodium bicarbonate. Washing with the aqueous alkaline solution can be at a temperature of less than 100° C., or less than 90° C., preferably 50-85° C. for a sufficient time. The mixture can be phase separated, and the purified biphenol dianhydride can be isolated to form a wet cake, and optionally washing the wet cake with water, a $C_{1-6}$ alcohol, or a combination thereof, preferably methanol, water, or a combination thereof, more preferably water. Phase separating the mixture and isolating the purified biphenol dianhydride composition can be by, for example, filtration, centrifugation, and the like, or a combination thereof. The aqueous alkaline solution can have a pH less than 14, preferably less than 10, more preferably 7.5 to 8.5. It is noted that contacting the solution with the aqueous alkaline solution at the temperatures indicated can induce crystallization of the biphenol dianhydride, and thus the resulting slurry can be washed with the aqueous alkaline solution.

In some embodiments, isolating the purified biphenol dianhydride can comprise adding an adsorbent to the solution to remove ionic species from the solution, and filtering the solution to remove the adsorbent and ionic species. The adsorbent can comprise, for example, celite, diatomaceous earth, silica, alumina, and the like, or a combination thereof. After contacting the biphenol dianhydride solution with the adsorbent, optionally with agitation, the solution can be filtered, preferably through a filter having a pore size of less than 40 to 60 micrometers to provide a solution comprising the biphenol dianhydride and being substantially free of the ionic species. As used herein, "substantially free" can refer to the solution comprising less than 25 ppm of ionic species.

In some embodiments, the slurry can have a solids content of 5 to 25 weight percent, preferably 7 to 25 weight percent, more preferably 7 to 15 weight percent. The solids content can affect whether a slurry or a solution results upon contact with the halogenated solvent. For example, a higher concentration (e.g., greater than 10%) may form a slurry at a given temperature, and at that same temperature, a lower concentration (e.g., less than 10%) may form a homogenous solution. In an embodiment wherein the contacting the biphenol dianhydride composition with the halogenated solvent is it a temperature and concentration effective to provide a solution, the method can further comprise adjusting the temperature of the solution to induce crystallization of the biphenol dianhydride composition to form the slurry, as discussed above.

In a specific embodiments, the method of making the biphenol dianhydride composition, the method of purifying the biphenol dianhydride composition, or both comprises contacting the biphenol dianhydride composition in a halogenated solvent as a slurry or solution with an aqueous alkaline solution to a temperature of less than 100° C., or less than 90° C., preferably 50-85° C. and a time of 5 minutes to 5 hours, preferably 15 minutes to 2 hours, more preferably 15 minutes to 55 minutes. Phase separating the mixture, isolating the purified biphenol dianhydride composition. Contacting the slurry or solution with an aqueous alkaline solution to remove ionic species from the slurry or solution. The ionic species can be one or more of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions. The aqueous alkaline solution can have a pH less than 14, preferably less than 10, more preferably 7.5 to 8.5. Phase separating the mixture and isolating the purified biphenol dianhydride composition can be by, for example, filtration, centrifugation, and the like, or a combination thereof. In an embodiment, isolating the purified biphenol dianhydride composition comprises filtering the slurry to form a wet cake, and optionally washing the wet cake with water, a $C_{1-6}$ alcohol, or a combination thereof, preferably methanol, water, or a combination thereof, more preferably water to provide the biphenol dianhydride composition substantially free of the ionic species. As used herein, "substantially free" can refer to the solution comprising less than 25 ppm of ionic species.

Advantageously, the biphenol dianhydride prepared or purified according to the above method can possess low levels of residual contaminants, in particular, low levels of ionic species. For example, the biphenol dianhydride can comprise less than 25 ppm each of sodium ions, potassium ions, calcium ions, zinc ions, aluminum ions, nickel ions, titanium ions, chromium ions, magnesium ions, manganese ions, copper ions, phosphorous ions, and iron ions. The biphenol dianhydride composition can comprise less than 175 ppm total of sodium ions, potassium ions, calcium ions, zinc ions, aluminum ions, nickel ions, titanium ions, chromium ions, magnesium ions, manganese ions, copper ions, phosphorous ions and iron ions. The biphenol dianhydride composition can comprise less than 35 ppm each of phosphate ions, sulfate ions, chloride ions, bromide ions, fluoride ions, nitrate ions, and nitrite ions. The biphenol dianhydride composition can comprise less than 50 ppm total of phosphate ions, sulfate ions, chloride ions, bromide ions, fluoride ions, nitrate ions, and nitrite ions.

The biphenol dianhydride made or purified by the methods described herein can advantageously be employed in a method of making a poly(etherimide). The method of making the poly(etherimide) can comprise contacting the biphenol dianhydride with one or more organic diamines in the presence of a halogenated solvent under conditions effective to provide the poly(etherimide).

The organic diamine can include 1,4-butane diamine, 1,5-pentanediamine, 1,6-hexanediamine, 1,7-heptanediamine, 1,8-octanediamine, 1,9-nonanediamine, 1,10-decanediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(p-amino-t-butyl) toluene, bis(p-amino-t-butylphenyl) ether, bis(p-methyl-o-aminophenyl) benzene, bis(p-methyl-o-aminopentyl) benzene, 1,3-diamino-4-isopropylbenzene, bis(4-aminophenyl) sulfide, bis-(4-aminophenyl) sulfone (also known as 4,4'-diaminodiphenyl sulfone (DDS)), and bis(4-aminophenyl) ether. Any regioisomer of the foregoing compounds can be used. $C_{1-4}$ alkylated or poly($C_{1-4}$)alkylated derivatives of any of the foregoing can be used, for example a polymethylated 1,6-hexanediamine. Combinations of these compounds can also be used. In some embodiments the organic diamine is m-phenylenediamine, p-phenylenediamine, o-phenylenediamine, 4,4'-diaminodiphenyl sulfone, 3,4'-diaminodiphenyl sulfone, 3,3'-diaminodiphenyl sulfone, 4,4'-oxydianiline, 3,4'-oxydianiline, 3,3'-oxydianiline or a combination thereof. In some embodiments, the diamine can comprise less than 25 ppm each of sodium ions, potassium ions, calcium ions, zinc ions, aluminum ions, titanium ions, phosphorus ions, and iron ions and less than 30 ppm each of phosphate ions, sulfate ions, chloride ions, nitrate ions, and nitrite ions. In some embodiments, the organic diamine can comprise less than 30 ppm each of various inorganic salts, for example, $NaHSO_3$, $Na_2SO_4$, $KHSO_3$, $K_2SO_4$, $NaNO_3$, $NaNO_2$, $KNO_3$, $KNO_2$, NaCl, KCl, $CaSO_4$, and $Ca(NO_3)_2$.

Conditions effective to provide the poly(etherimide) can include a temperature of 170 to 380° C., and a solids content of 10 to 50 weight percent, preferably 20 to 40 weight percent, more preferably 25 to 35 weight percent. Polymerizations can be carried out for 2 to 24 hours, preferably 3 to 6 hours. The polymerization can be conducted at reduced, atmospheric, or high pressure.

The method can also optionally employ various chain stoppers or end capping agents, and thus the poly(etherimide) can optionally further comprise at least one chain end derived from a chain stopper. The chain stopper limits molecular weight growth rate and thus can be used to control molecular weight in the poly(etherimide). Exemplary chain stoppers include certain mono amines (for example aniline), mono anhydrides (for example phthalic anhydride), monophenolic compounds and the like. In some embodiments, the chain stopper can preferably be a monoamine chain stopper or a monoanhydride chain stopper, more preferably aniline or phthalic anhydride. It should be understood however that the poly(etherimides) disclosed herein can be produced having any desired weight average molecular weight (Mw) with any end cap.

In some embodiments, the organic diamines, the chain stoppers (when present), or both can possess low levels of inorganic contaminants, for example less than 50 ppm or less than 25 ppm each of phosphate ions, sulfate ions, chloride ions, nitrate ions, and nitrite ions.

In some embodiments, no catalysts are used in the polymerization of the poly(etherimide).

The method of making the poly(etherimide) can optionally further comprise a devolatilization step. Low levels of residual volatile species in the final polymer product can be achieved by devolatilization, and devolatilization can also serve to finish the end groups in the polymer product. In some embodiments the bulk of any solvent may be removed and any residual volatile species may be removed from the polymer product by devolatilization, optionally at reduced pressure. In other embodiments the polymerization reaction is taken to some desired level of completion in solvent and then the polymerization is essentially completed during at least one devolatilization step following the initial reaction in solution. Apparatuses to devolatilize the polymer mixture and reduce solvent and other volatile species to the low levels needed for good melt processability are generally capable of high temperature heating under vacuum with the ability to rapidly generate high surface area to facilitate removal of the volatile species. The mixing portions of such apparatuses are generally capable of supplying sufficient power to pump, agitate and stir the high temperature, amorphous poly(etherimide) melt which may be very viscous. Suitable devolatilization apparatuses include, but are not limited to, wiped films evaporators and devolatilizing extruders, especially twin screw extruders with multiple venting sections. In some embodiments, the method can optionally further comprise devolatilizing the poly(etherimide) at 335 to 425° C., preferably at 360 to 400° C., even more preferably at 375-390° C. for 1 to 30 minutes.

The poly(etherimide) prepared according to the method described herein and using the biphenol dianhydride made or purified according to the present disclosure can advantageously have low levels of residual impurities. In particular, the poly(etherimide) can comprise less than 25 ppm each of sodium ions, potassium ions, calcium ions, zinc ions, aluminum ions, and iron ions, nickel ions, chromium ions, magnesium ions, manganese ions, titanium ions, copper ions, phosphorus ions and less than 35 ppm each of phosphate ions, sulfate ions, chloride ions, nitrate ions, bromide ions, fluorides ions, and nitrite ions.

Poly(etherimides) prepared according to the method of the present disclosure can be particularly useful for forming various articles. The poly(etherimide) can be formed into articles using any suitable technique, for example, melt-processing techniques. Melt-molding methods can include injection molding, extrusion molding, blow molding, rotational molding, coining, and injection blow molding. For example, the melt molding method can be injection molding. The poly(etherimide) can be formed into sheets or films by casting, blowing, or extruding. These can be further thermoformed into articles and structures that can be oriented from the melt or at a later stage in the processing of the compositions. The poly(etherimide) can be over-molded onto an article made from a different material or by a different process. The articles can also be formed using techniques such as compression molding or ram extruding. The articles can be further formed into other shapes by machining. Exemplary articles include a fiber, a film, a sheet, a foam, a filament, a molded article, an extruded article, or a powder. The poly(etherimide) of the present disclosure can also be particularly suitable for use in optoelectronic applications. In particular, the poly(etherimide) can be used for optoelectronic articles such as transmitters, receivers, connectors, lenses, waveguides, and the like.

Accordingly, methods for the preparation and purification of a biphenol dianhydride having low levels of residual contaminants are provided herein. The biphenol dianhydrides of the present disclosure can be used in the preparation of rigid, high molecular weight biphenyl-containing poly(etherimides) which can be particularly useful for various applications, for example in optical articles. Thus, a significant improvement is provided by the present disclosure.

This disclosure is further illustrated by the following examples, which are non-limiting.

EXAMPLES

Materials used in the following examples are provided in Table 1.

TABLE 1

| Material | Chemical Description |
| --- | --- |
| N,N'-Ph-3,3'-BPoBI | N,N'-phenyl-3,3'-biphenol diphthalimide |

TABLE 1-continued

| Material | Chemical Description |
|---|---|
| N,N'-Ph-3,4'-BPoBI | N,N'-phenyl-3,4'-biphenol diphthalimide |
| N,N'-Ph-4,4'-BPoBI | N,N'-phenyl-4,4'-biphenol diphthalimide |
| 3,3'-BPoTA•4Na | 3,3'-biphenol diphthalic acid sodium salt |
| 3,3'-BPoTA | 3,3'-biphenol diphthalic acid (3,3'-biphenol tetraacid) |

TABLE 1-continued

| Material | Chemical Description |
|---|---|
| 3,4'-BPoTA | 3,4'-biphenol diphthalic acid (3,4'-biphenol tetraacid) |
| 4,4'-BPoTA | 4,4'-biphenol diphthalic acid (4,4'-biphenol tetraacid) |
| BPoAnhDA | biphenol anhydride diacid |
| 3,3'-BPoDA | 3,3'-biphenol diphthalic anhydride |

TABLE 1-continued

| Material | Chemical Description |
| --- | --- |
| 3,4'-BPoDA | 3,4'-biphenol diphthalic anhydride |

[Chemical structure of 3,4'-biphenol diphthalic anhydride]

| 4,4'-BPoDA | 4,4'-biphenol diphthalic anhydride |

[Chemical structure of 4,4'-biphenol diphthalic anhydride]

| 4,4'-DDS | 4,4'-Diaminodiphenyl sulfone |
| p-PD | Para-phenylene diamine |
| 4,4'-ODA | 4,4'-oxydianiline |
| Tn-PD | Meta-phenylene diamine |
| PA | Phthalic Anhydride |
| o-DCB | Ortho-dichlorobenzene |
| DI Water | Deionized water |
| SDBS | sodium dodecylbenzene sulfonate |

All polymer molecular weights in the following examples are determined by gel permeation chromatography (GPC) with respect to polystyrene standards unless otherwise noted.

All ultra-performance liquid chromatography (UPLC) analyses in the following examples were performed on a Waters ACQUITY UPLC BEH C18 1.7 μm 2.1×50 mm column at 35° C. PDA detection was performed at 254 nm with a flow rate of 0.313 mL/min. A gradient method was used with a dual solvent system of acetonitrile and acidic water (4 L DI $H_2O$+3 mL 85% $H_3PO_4$). It is noted that UPLC analysis of BPoDA shows small amounts of BPoAnhydride-Diacid ("BPoAnhDA") due to partial hydrolysis that occurs during analysis.

All residual levels of metals (sodium, potassium, calcium, zinc, aluminum, iron, nickel, titanium, chromium, magnesium, manganese, copper, phosphorus) in the following examples are determined by an inductively coupled plasma-digestion (ICP-Dig) method which uses an ICP spectrometer equipped with: an axial and/or radial viewing, a Gem Cone and/or Ultrasonic nebulizer, and a microwave digestion system equipped with appropriate sample digestion vessels set. Samples are prepared using concentrated nitric acid, hydrochloric acid, sulfuric acid, and/or hydrofluoric acid—Supra pure grades.

Residual levels of anions (sulfates, chlorides, bromides, fluorides, phosphates, nitrates, nitrites) present in BPoDA and poly(etherimide) samples were measured by extraction-ion chromatography (IC-Extract). The BPoDA samples were dissolved in methylene chloride and the poly(etherimide) samples were dissolved in methylene chloride with hexafluoroisopropanol (HFIP) added to help with solubility. The solutions were then extracted with deionized water, and then the aqueous extracts were analyzed using a calibrated Dionex ICS 2000 instrument.

Residual levels of anions (sulfates, chlorides, bromides, fluorides, phosphates, nitrates, nitrites) present in BPoTA samples were measured by total ion chromatography combustion (IC-Total) using a calibrated Dionex ICS 2000 instrument.

DSC measurements of the polymer sample (5 milligrams) were performed with a TA Q1000 DSC instrument. The film samples were scanned from 40-300° C. under nitrogen atmosphere. The glass transition temperature (Tg), and the melting temperature (Tm) of the polymers were determined from the second heating scan. Heating rate of 20° C./min was used in these experiments.

Example 1

A hydrolysis vessel containing DI water (260 kg) was charged with N,N'-phenyl-biphenol bisimide (N,N'-Ph-BPoBI) (a mixture of N,N'-Ph-3,3'-BPoBI, N,N'-Ph-3,4'-BPoBI, N,N'-Ph-4,4'-BPoBI) wet cake (268 kg total mass). The reactor was agitated at 90% power and heated to 90° C. with a nitrogen purge. A solution of 50% aqueous NaOH (60.80 kg, 760 mol, 8.0 equiv.) was then added to make a total reactor mass of 330 kg. The vessel was sealed and heated for three hours until the internal pressure reached 130-135 psig (180° C.). The pressure was maintained at 130-135 psig for an additional five hours, and then the set temperature was adjusted to 85-90° C. Agitation was also decreased to 60% power. The vessel was carefully depressurized to 2 psig and a sample was taken. UPLC analysis indicated that the hydrolysis to the corresponding tetraacid was complete.

A wash vessel was charged with o-DCB (225 kg), agitated, and heated to 90-95° C. The aqueous solution of BPoTA•4Na was transferred into the wash vessel, agitated at 50% power for 30 minutes, then the layers were allowed to separate. After 45 minutes, the bottom layer, containing small amount of precipitated BPoTA•4Na, o-DCB and aniline, was transferred to Nutsche filter and then drained to waste. The top layer, containing BPoTA•4Na in water, remained heating at 90-95° C. The washing step with o-DCB was repeated once more to remove aniline.

A quench vessel was charged with DI water (170 kg), agitated, then charged with 50% aqueous $H_2SO_4$ (112 kg, 570 mol, 6 equiv.) via a Teflon-lined drum pump with a PVC flexible hose. The transfer lines were flushed with DI water (20 kg) and sent into the quench vessel to achieve a total mass of 302 kg. The aq. $H_2SO_4$ was then heated to 90-95° C. with 80% agitation power prior to quench. The aqueous solution in of BPoTA•4Na in the wash vessel, held at 90-95° C., was transferred to the quench vessel over the course of 90 minutes. The wash vessel was then rinsed with DI water (60 kg), reheated to 90-95° C., and the rinse was also sent into the quench vessel. The resultant milky mixture was agitated at 80% power. The quench reactor was blocked in at 90-95° C., and the contents were held overnight to ensure full protonation of carboxylate species. The solids settled quickly from the aqueous media. Afterwards, the slurry was cooled down to 80-85° C.

A Teflon-lined flexible hose and fittings with the appropriate compatible material of construction was used to transfer the slurry to a 40 liter Nutsche filter, containing a 60 um Teflon filter media. Under 50 psig, the liquid was separated from the solids in the Nutsche filter and the filtrate was sent into a polypropylene tote. After the filtration was completed, the transfer process was repeated until the product cake filled the bottom section of the Nutsche filter. The filter was then depressurized. A hold tank was filled with DI water, heated to 90° C., and pressurized to 50 psig. Water was then transferred from the hold tank to the Nutsche filter, and then the system was closed and allowed to soak for 30 minutes. The Nutsche filter was then pressurized to remove the water. This batch-flushing protocol was repeated several times. As before, the filtrate was sent into a polypropylene tote. The waste stream was monitored until a pH of 2.9 or higher was obtained. The water flow was then halted, the filter was pressurized to 50 psig to remove most of the water, and the wet cake was finally transferred into a plastic drum. This cake isolation procedure was continued until all BPoTA was collected. The pan solids analysis of cake indicated wt % solids in the range of 90-95%. A total of 29.00 kg of the white BPoTA wet cake was isolated with an estimated dry mass of 27.26 kg. The combined wet cakes were used directly in the ring-closure step without further drying. ICP-Dig: sodium (25), potassium (0.71 ppm), calcium (1.4 ppm), aluminum (2.1 ppm), iron (2.2 ppm), titanium (0.16 ppm), phosphorus (7.2 ppm); IC-Extract: sulfates (81.32 ppm), chlorides (0.8 ppm) and IC-Total: sulfates (242 ppm), chlorides (1818 ppm); UPLC: 3,3'-BPoTA+isomers (96.96%), with small levels of 3,4'- and 4,4'-isomers and unknown impurity (2.53%).

The combined BPoTA wet cakes (27.26 kg dry basis, 53.02 mol), o-DCB (535 kg) and acetic anhydride (73 kg) were charged into the vessel to make 3.5 wt % mixture. Nitrogen was applied, the mixture was agitated, and then the contents were heated to 125-130° C. and maintained at this temperature for 4-5 hours. A UPLC analysis on the reactor sample indicated that cyclization to BPoDA was complete. After overnight temperature of 125-130° C., the temperature was increased to 180-185° C. and the reactor content was concentrated to a total mass of 250 kg (9-10 wt % solids). At this point, all solids dissolved to form a yellow solution and a sample of the overheads was determined to contain <21 ppm of water by Karl-Fisher analysis. The temperature of the vessel was then adjusted to 75-80° C. to allow for recrystallization of 3,3'-BPoDA product. A sample was then visually inspected and showed the formation of white-to-light beige colored precipitate formation having good flow with no tackiness. The recrystallized product was filtered in the Nutsche filter by connecting a flex hose from ring-closure vessel to filter. The Nutsche filter was cleaned with o-DCB (5 gal), dried, and affixed with a 60 micrometer Nomex filter media. The BPoDA slurry in o-DCB was then transferred to the Nutsche filter with a slight nitrogen pressure and the first cake was formed.

The cake was washed by filling in the Nutsche filter with DI water at 80-85° C., then the system was closed and allowed to soak for 30 minutes. The filter was then pressurized to remove the water. This step was repeated once more. After removing water, the product was then washed with room temperature methanol. This protocol was repeated until all BPoDA product was isolated. The wet cakes were placed into aluminum foil pans and dried in a vacuum oven at 140-145° C. (30 inches Hg) until a consistent mass was obtained. A total of 18.28 kg of BPoDA isomers was obtained as a light beige colored solid. $DSC_{(melt)}$=281-282° C.; UPLC: 3,3'-BPoDA+isomers (99.19%), an unknown peak (0.81%); ICP-Dig: sodium (24.5 ppm), potassium (3.6 ppm), aluminum (2.1 ppm), iron (3.6 ppm), titanium (2.4 ppm), phosphorus (5.2 ppm); IC-Extract: sulfates (1.01 ppm), chlorides (<0.5 ppm), phosphates (<0.5 ppm), nitrates (<0.5 ppm), nitrites (<0.5 ppm).

Example 2

BPoTA was prepared as described in Example 1. The BPoTA wet cake obtained in Example 2 had a solids content in the range of 85-90%. A total of 46.58 kg of the white BPoTA wet cake was isolated with an estimated dry mass of 39.60 kg. The wet cake was used directly in the ring-closure step without further drying. ICP-Dig: sodium (139 ppm), potassium (9 ppm), zinc (5 ppm), calcium (5 ppm), aluminum (2 ppm), iron (8 ppm), titanium (0 ppm), phosphorus (9 ppm); IC-Extract: sulfates (75.08 ppm), chlorides (<0.5 ppm), phosphates (<0.5 ppm), fluorides (<0.5 ppm); IC-Total: sulfates (288 ppm), phosphates (<20 ppm), chlorides (863 ppm), fluorides (<20 ppm); UPLC: 3,3'-BPoTA+isomers (97.10%), with small levels of 3,4'- and 4,4'-isomers and unknown impurity (1.80%).

The BPoTA wet cake (39.60 kg dry basis, 76.98 mol) and o-DCB (180 kg) was charged into the vessel to make 17 wt % mixture. Nitrogen was applied, the mixture was agitated, and then the contents were heated to 180-185° C. and maintained at this temperature for 3-4 hours. A UPLC analysis on the reactor sample indicated that cyclization to BPoDA was complete. The reactor content was then concentrated to a total mass of 170 kg (21-22 wt % solids). A sample of the overheads was analyzed for water content. The Karl-Fisher analysis showed 35 ppm of water. The temperature of the vessel was then lowered to 75-80° C. to allow for recrystallization of 3,3'-BPoDA product. A sample was then visually inspected and showed the formation of light beige colored precipitate having good flow with no tackiness. The recrystallized product was filtered in the Nutsche filter by connecting a flex hose from ring-closure vessel to filter. The Nutsche filter was cleaned with o-DCB (5 gal), dried, and affixed with a 60 micrometer Nomex filter media. The BPoDA slurry in o-DCB was then transferred to the Nutsche filter with a slight nitrogen pressure and the first cake was formed.

The cake was washed by filling in the Nutsche filter with DI water at 80-85° C., then the system was closed and allowed to soak for 30 minutes. The filter was then pressurized to remove the water. This step was repeated once more. After removing water, the product was then washed with room temperature methanol. This protocol was repeated until all BPoDA product was isolated. The wet cakes were placed into aluminum foil pans and dried in a vacuum oven at 140-145° C. (30 inches Hg) until a consistent mass was obtained. A total of 23.80 kg of BPoDA was obtained as a light-beige colored solid. UPLC: 3,3'-BPoDA+isomers (99.25%), an unknown peak (0.75%); ICP-Dig: sodium (147 ppm), potassium (7.3 ppm), calcium (9.4 ppm), aluminum (1.6 ppm), iron (6.4 ppm), titanium (0.34 ppm), phosphorus (10.5 ppm); IC-Extract: sulfates (8.22 ppm), chlorides (<0.5 ppm), phosphates (<0.5 ppm), nitrates (<0.5 ppm), nitrites (0.5 ppm).

Example 3

The 3,3'-BPoDA isolated above (Comparative Example 2) was charged back (in three batches, each with 8-9 kg of DA on a dry basis) into Nutsche filter and was filed with 85-90° C. DI water, and then the system was closed and allowed to soak for 30 minutes. The Nutsche filter was then pressurized to remove the water. This batch-flushing protocol was repeated 5-6 times. As before, the filtrate was sent into a polypropylene tote. The filter was pressurized to 50 psig for few hours to remove majority of the water, and the wet cake was finally transferred into a plastic drum. This cake isolation procedure was continued until all BPoDA was re-washed. The pan solids analysis of cake indicated wt % solids in the range of 88-94%. UPLC: 3,3'-BPoDA+isomers (99.20%); ICP-Dig: sodium (114 ppm), potassium (11 ppm), calcium (1 ppm), aluminum (1.07 ppm), iron (15 ppm), nickel (5 ppm), chromium (12 ppm), phosphorus (9 ppm); IC-Extract: sulfates (9.1 ppm), chlorides (3.6 ppm), phosphates (11.7 ppm), nitrates (<0.5 ppm), nitrites (<0.5 ppm), bromides (<0.5 ppm), fluorides (<0.5 ppm).

Example 4

A Parr reactor was charged with aq. sodium hydroxide (20.36 g, 50 mass %, 254.5 mmol, 8 equiv.), water (75 g, 75 mL), and N,N'-Ph-BPoBI (a mixture of N,N'-Ph-3,3'-BPoBI, N,N'-3,4'-BPoBI, N,N'-4,4'-BPoBI isomers) (20 g, 31.8 mmol, 1 equiv.) in 75 ml o-DCB. The reactor was sealed, degassed 10 times with nitrogen, and then heated to 180° C. (135 psig). After 40-45 minutes, the internal pressure reached 130-131 psig (180° C.). The reaction continued at this temperature and pressure for 2-3 hours, and after three hours the reactor was cooled to 90° C. After carefully depressurizing the Parr reactor, UPLC analysis of the mixture showed that all starting material was consumed.

Next, the mixture was poured into a preheated (90° C.) separatory funnel and the layers were separated within 3-5 minutes. The organic layer containing small precipitate was removed and discarded from the aqueous layer containing 3,3'-BPoTA•4Na. The aqueous layer was washed with fresh, hot o-DCB (4×100 mL, 90° C.) to remove aniline. After each wash, the layers were separated within 3-5 minutes.

A 500 mL 3-neck round-bottom flask with mechanical stirrer, Dean-Stark trap, condenser, and addition funnel was charged with hydrochloric acid (31.32 g, 26.10 mL, 27 mass %, 310.8 mmol) and water (50 g), then heated to 90° C. The BPoTA•4Na solution (hot) prepared above was placed in the heated addition funnel and was then added dropwise to the aq. hydrochloric acid over 30 minutes. An off-white solid precipitate was immediately observed. Additional water (30 mL) was used to rinse the addition funnel, and added to the quench vessel. After the addition was complete, the mixture was heated for an additional 2 hours to fully protonate the carboxylate groups. The product was collected by hot filtration and then washed with hot DI water (2×200 mL). The product was allowed to dry in the vacuum oven at 90° C. until a consistent mass was obtained. In this manner 13.57 g of the 3,3'-BPoTA product was collected in 83% yield and 95.7% purity. ICP-Dig: sodium (52 ppm), potassium (6.8 ppm), zinc (16.7 ppm), calcium (31 ppm), aluminum (7.4 ppm), iron (7.7 ppm), titanium (2.5 ppm), phosphorus (27 ppm).

In a 250 mL 3-neck round-bottom flask with mechanical stirrer, Dean-Stark trap and condenser was placed above 3,3'-BPoTA (6 g, 11.66 mmol) and o-DCB (11 g, 8 mL). The flask was then placed in an oil bath at 185° C. under nitrogen. The fresh o-DCB was added to the reaction flask to make up the solvent loss in the Dean-Stark trap. After three hours, UPLC analysis indicated the reaction was complete and a light-beige colored precipitate in o-DCB was observed. The mixture was then cooled to 70-75° C. The product was collected by hot filtration and then washed with hot DI water (2×20 mL). The product was allowed to dry in the vacuum oven at 140-145° C. until a consistent mass was obtained. In this manner, 4.59 g of the 3,3'-BPoDA product was collected in 81.5% yield and 97.01% purity. ICP-Dig: sodium (23.5 ppm), potassium (11 ppm), zinc (22.5 ppm), calcium (32.5 ppm), aluminum (11.7 ppm), iron (6.4 ppm), titanium (0.13 ppm), phosphorus (23 ppm).

Example 5

A Parr reactor was charged with aq. sodium hydroxide (20.36 g, 50 mass %, 254.5 mmol, 8 equiv.), water (75 g, 75 mL), sodium dodecylbenzene sulfonate (SDBS) (1.35 g, 1.59 mmol, 0.05 mol %) and N,N'-Ph-BPoBI (a mixture of N,N'-Ph-3,3'-BPoBI, N,N'-3,4'-BPoBI, N,N'-4,4'-BPoBI isomers) (20 g, 31.8 mmol, 1 equiv.). The reactor was sealed, degassed 10 times with nitrogen, and then heated to 180° C. (135 psig). After 40 minutes, the internal pressure reached 130-131 psig (180° C.). The reaction continued at this temperature and pressure for 2-3 hours, and after three hours the reactor was cooled to 90° C. After carefully depressurizing the Parr reactor, UPLC analysis of the mixture showed all starting material was consumed.

Next, the mixture was poured into a preheated (90° C.) separatory funnel and the layers were separated within 3-5 minutes. The organic layer containing small precipitate was removed and discarded from the aqueous layer containing 3,3'-BPoTA•4Na. The aqueous layer was washed with fresh, hot o-DCB (3×80 mL, 90° C.) to remove aniline. After each wash, the layers were separated within 3-5 minutes.

A 500 mL 3-neck round-bottom flask with mechanical stirrer, Dean-Stark trap, condenser, and addition funnel was charged with sulfuric acid (25 g, 13.59 mL, 95-98 mass %, 254.9 mmol) and water (150 g), then heated to 90° C. The TA•4Na solution (hot) prepared above was placed in the heated addition funnel and was then added dropwise to the aq. sulfuric acid over 30 minutes. A light-beige colored precipitate was immediately observed. Additional water (30 mL) was used to rinse the addition funnel, and added to the quench vessel. After the addition was complete, the mixture was heated for an additional 30 minutes to fully protonate the carboxylate groups. The product was collected by hot filtration and then washed with hot DI water (3×400 mL). The product was allowed to dry in the vacuum oven at 90° C. until a consistent mass was obtained. In this manner 15.04 g of the 3,3'-BPoTA product was collected in 91.98% yield. ICP-Dig: sodium (92 ppm), potassium (4.3 ppm), zinc (3.0 ppm), calcium (7.5 ppm), aluminum (2.6 ppm), iron (7.0 ppm), titanium (0.31 ppm), phosphorus (6.2 ppm).

In a 250 mL 3-neck round-bottom flask with mechanical stirrer, Dean-Stark trap and condenser was placed above 3,3'-BPoTA (6 g, 11.66 mmol) and o-DCB (18 g, 14 mL). The flask was then placed in an oil bath at 185° C. under nitrogen. The fresh o-DCB was added to the reaction flask to make up the solvent loss in the Dean-Stark trap. After 3 hours, UPLC analysis indicated the reaction was complete and a light-beige colored precipitate in o-DCB was observed. The mixture was then cooled to 70-75° C. The product was collected by hot filtration and then washed with hot DI water (2×20 mL). The product was allowed to dry in the vacuum oven at 140-145° C. until a consistent mass was obtained. In this manner, 4.49 g of the 3,3'-BPoDA product was collected in 80.5% yield. UPLC: 3,3'-BPoDA+isomers (98%); ICP-Dig: sodium (21.6 ppm), potassium (9 ppm), zinc (6.7 ppm), calcium (16.4 ppm), aluminum (6.4 ppm), iron (4.6 ppm), titanium (0 ppm), phosphorus (21 ppm).

Example 6

A 500 mL 3-necked round bottom flask equipped with Dean-Stark trap and condenser was charged with N,N'-Ph-BPoBI (a mixture of N,N'-Ph-3,3'-BPoBI, N,N'-3,4'-BPoBI, N,N'-4,4'-BPoBI isomers) (20.0 g, 31.8 mmol), 50% (wt/wt) aqueous NaOH (20.36 g, 254.5 mmol, 8 equiv.) and ethylene glycol (85 g, 76 mL). The mixture was heated to 150° C. under nitrogen atmosphere for 5 hours. The, the temperature was raised to 180° C. and maintained at this condition for 8 hours. UPLC analysis indicated that the starting material was consumed. The reaction mixture turned white with slight yellow tint as the reaction progressed. Aniline was removed under reflux. Then, the heat was removed and the content was diluted with ethylene glycol (50 mL) to facilitate filtration. The filtration was performed once the content was cooled to room temperature. The cake was then reslurried with DI water (120 mL). The resulting aqueous mixture containing 3,3'-BPoTA•4Na was then transferred to an addition funnel for the quenching procedure.

A 1000 mL 3-neck round bottom flask equipped with a mechanical stirrer and condenser was charged with water (150 mL) and conc. (95-98%) $H_2SO_4$ (20.351 mL, 381.78 mmol, 12.0 equiv.). The flask was heated to 90° C., the addition funnel was attached, and the aqueous solution of BPoTA•4Na was added drop wise over 30 min. An off-white colored solid was precipitated immediately. After the addition was complete, the mixture was heated for an additional 2 hours to fully protonate the carboxylate groups. The solid was collected by hot filtration and washed with water (4×250 mL). The cake was dried in an oven at 80-90° C. under vacuum (0.8 inches Hg) until no change in mass was seen. In this manner, 13.40 g of the 3,3'-BPoTA product was collected in 82.0% yield. UPLC analysis indicated 3,3'-BPoTA (95.12%), 3,4'-BPoTA (0.25%), minor unknown peaks were present. ICP-Dig: sodium (89 ppm), potassium (7.2 ppm), zinc (14 ppm), calcium (20.4 ppm), aluminum (10.3 ppm), iron (4.7 ppm), titanium (1.1 ppm), phosphorus (8.2 ppm).

In a 250 mL 3-neck round-bottom flask with mechanical stirrer, Dean-Stark trap and condenser was placed above 3,3'-BPoTA (6 g, 11.66 mmol) and o-DCB (7 g, 5.3 mL). The flask was then placed in an oil bath at 185° C. under nitrogen. The fresh o-DCB was added to the reaction flask to make up the solvent loss in the Dean-Stark trap. After three hours, UPLC analysis indicated the reaction was complete and a light greenish colored precipitate in o-DCB was observed. The mixture was then cooled to 70-75° C. The product was collected by hot filtration and then washed with hot DI water (2×30 mL). The product was allowed to dry in the vacuum oven at 140-145° C. until a consistent mass was obtained. In this manner, 4.63 g of the 3,3'-BPoDA product was collected in 83% yield and 96.7% purity. ICP-Dig: sodium (16 ppm), potassium (8.1 ppm), zinc (3.8 ppm), calcium (13 ppm), aluminum (5.5 ppm), iron (5.4 ppm), titanium (0 ppm), phosphorus (19 ppm).

Example 7

A Parr reactor was charged with aq. sodium hydroxide (15.27 g, 50 mass %, 191 mmol, 8 equiv.), water (75 g, 75 mL), and N,N'-Ph-BPoBI (a mixture of N,N'-Ph-3,3'-BPoBI, N,N'-3,4'-BPoBI, N,N'-4,4'-BPoBI isomers) (15 g, 23.86 mmol, 1 equiv.). The reactor was sealed, degassed 10 times with nitrogen, and then heated to 180° C. (135 psig). After 35 minutes, the internal pressure reached 130-131 psig (180° C.). The reaction continued at this temperature and pressure for 5 hours, and then the reactor was cooled to 90° C. After carefully depressurizing the Parr reactor, UPLC analysis of the mixture showed all starting material was consumed.

Next, the mixture was poured into a preheated (90° C.) separatory funnel and the layers were separated within 3-5 minutes. The organic layer containing small precipitate was removed and discarded from the aqueous layer containing 3,3'-BPoTA•4Na. The aqueous layer was washed with fresh, hot o-DCB (3×70 mL, 90° C.) to remove aniline. After each wash, the layers separated within 3-5 minutes.

A 500 mL 3-neck round-bottom flask with mechanical stirrer, Dean-Stark trap, condenser, and addition funnel was charged with phosphoric acid (27.50 g, 14.78 mL, 85 mass %, 238.6 mmol) and water (100 g), then heated to 90° C. The TA•4Na solution (hot) prepared above was placed in the heated addition funnel and was then added dropwise to the aq. phosphoric acid over 30 minutes. A dull gray colored precipitate was immediately observed. Additional water (30 mL) was used to rinse the addition funnel, and added to the quench vessel. After the addition was complete, the mixture was heated for an additional 60 minutes to fully protonate the carboxylate groups. The product was collected by hot filtration and then washed with hot DI water (3×400 mL). The product was allowed to dry in the vacuum oven at 90° C. until a consistent mass was obtained. In this manner 9.73 g of the 3,3'-BPoTA product was collected in 79.29% yield. ICP-Dig: sodium (79 ppm), potassium (5.8 ppm), zinc (5.7 ppm), calcium (9.7 ppm), aluminum (17.6 ppm), iron (8.9 ppm), titanium (1.4 ppm), phosphorus (464 ppm).

In a 250 mL 3-neck round-bottom flask with mechanical stirrer, Dean-Stark trap and condenser was placed 3,3'-BPoTA (6 g, 11.66 mmol), o-DCB (120 g, 92 mL), and acetic anhydride (8.6 g, 85.19 mmol). The flask was then heated to 130-135° C. under nitrogen. The reaction was maintained at this temperature for 3 hours, and then the temperature was increased to 185° C. The fresh o-DCB was added to the reaction flask to make up the solvent loss in the Dean-Stark trap. After four hours, UPLC analysis indicated the reaction was complete. The resulting homogenous solution was cooled to 70-75° C. to form a light gray colored precipitate in o-DCB. The product was collected by hot filtration and then washed with hot DI water (2×30 mL). The product was allowed to dry in the vacuum oven at 140-145° C. until a consistent mass was obtained. In this manner, 4.75 g of the 3,3'-BPoDA product was collected in 86.0% yield. UPLC: 3,3'-BPoDA+isomers (97.90%); ICP-Dig: sodium (22 ppm), potassium (9.1 ppm), zinc (6.9 ppm), calcium (20.3 ppm), aluminum (6.1 ppm), iron (4.2 ppm), titanium (0.19 ppm), phosphorus (22 ppm).

Polymer molecular weights in the following examples were determined by gel permeation chromatography (GPC)) analysis with a Water 2695 Separations Module equipped with a Polymer Lab Pigel 5 micrometer MIXED-C column and Waters 2487 PDA detector at 254 nm. Elution was effected with an isocratic solvent system of dichloromethane at 1 mL/min and polymer molecular weights were reported relative to polystyrene standards.

Comparative Example 8

The following procedure used 3,3'-BPoTA which had the following profile: ICP-Dig: sodium (220 ppm), potassium (6 ppm), zinc (4 ppm), calcium (10 ppm), aluminum (6 ppm), iron (10 ppm), titanium (0 ppm), phosphorus (5 ppm), nickel (3 ppm), magnesium (4 ppm), copper (1 ppm), chromium (24 ppm); IC-Total: fluoride (<20 ppm), chlorides (972 ppm), nitrites (400 ppm), bromides (<20 ppm), nitrates (1232 ppm), sulfates (796 ppm), phosphates (<20 ppm); IC-Extract: sulfates (201.8 ppm), chlorides (1.1 ppm), phosphates (<0.5 ppm), nitrates (1.2 ppm), nitrites (<0.5 ppm), bromides (<0.5 ppm), fluorides (<0.5 ppm).

A 500 mL 3-neck round bottom flask with mechanical stirrer, Dean-Stark trap, condenser and nitrogen inlet was charged with 3,3'-BPoTA (50.01 g, 97.22 mmol), DI water (20 g), and o-DCB (215 g). The flask was heated at 180° C. with 150 rpm agitation. After two hours and 30 minutes, 17 g of distillate was removed from the trap. The contents were heated overnight and then the oil bath temperature was adjusted to 200° C. After a total heating time of 23.5 hours, UPLC analysis indicated that >99% of the starting material had ring-closed to form 3,3'-BPoDA and the mixture was cooled to ambient temperature.

The mixture was then reheated to 90° C. and an aqueous solution of 3 wt % sodium bicarbonate, heated to 90° C., was added to the flask. After agitating vigorously for 15 minutes, the mixture was poured into a 1000 mL separatory funnel and the layers were allowed to separate. The aqueous and rag layers were removed and discarded. The organic layer was then washed twice with DI water (2×100 mL) heated to 85-90° C. The resulting organic slurry was filtered through a Buchner funnel containing a #4 Whatman filter paper. The solids were dried further in a vacuum oven at 140° C. overnight to provide 3,3'-BPoDA (30.61 g,) in 65.8% yield. UPLC: 3,3'-BPoDA+isomers (97%); ICP-Dig: sodium (200 ppm), potassium (8 ppm), zinc (5 ppm), calcium (15 ppm), aluminum (6 ppm), iron (9 ppm), titanium (0 ppm), phosphorus (6 ppm), chromium (16 ppm), copper (1 ppm), magnesium (5 ppm), nickel (3 ppm); IC-Extract: sulfates (15.5 ppm), chlorides (0.50 ppm), phosphates (<0.5 ppm), nitrates (1.70 ppm), nitrites (<0.5 ppm).

Example 9

To a solution of N,N'-Ph-BPoBI (a mixture of N,N'-Ph-3,3'-BPoBI, N,N'-3,4'-BPoBI, N,N'-4,4'-BPoBI isomers) in o-DCB (260 kg at 16-17 wt % solids) was added DI water. The reactor was agitated at 90% power with a nitrogen purge. A solution of 50% aqueous NaOH (45.98 kg, 575.20 mol, 6.0 equiv.) was then added hydrolysis vessel. The contents (640 kg) were then sealed with the nitrogen regulator set to 10 psig and heated over the next three hours until the internal pressure reached 130-135 psig (180° C.). The pressure was maintained at 130-135 psig for an additional 4-5 hours with agitation. The contents were cooled to 85-90° C. and the vessel was carefully depressurized to 2 psig after which a sample was taken for stoichiometry determination. UPLC analyses of the reaction mixture showed that hydrolysis was complete.

Agitation was ceased and the layers were allowed to separate over 60 minutes while maintaining an internal temperature of 90-95° C. The bottom (o-DCB/aniline/small amount of precipitated BPoTA•4Na) layer was sent through a bag filter and drained within 20 minutes. Then, another 170 kg of hot DI water was added to help phase separate. The bottom layer sent through a filter was discarded to waste. At this point the reaction vessel contained a top layer comprising $H_2O$, aniline and BPoTA•4Na at approximately 9-10 wt % solids. The top layer containing product in water was heated to 120-125° C. with 50% agitation.

A hold tank was charged with DI water, which was then heated to 95° C. and sent to the hydrolysis vessel as needed to maintain 350 kg weight (16 wt % solids) in the reactor as the azeotrope distilled out at 120-125° C. Overheads were monitored every 30 minutes for the presence of aniline. Agitation was reduced to 20% power and the tempered oil was reduced to 120° C. Removal of the aniline byproduct was monitored using UPLC analysis of the reactor sample. The weight of the vessel was maintained 350 kg to keep the BPoTA•4Na dissolved. Next, the solution was maintained at 90° C. with agitation.

A quench vessel was charged with DI water (120 kg), agitated without heat, and then charged with 50% aqueous $H_2SO_4$ (62.05 kg, 316.3 mol, 3.3 equiv.) via a Teflon-lined drum pump with a PVC flexible hose. The transfer lines were subsequently flushed with DI water (20 kg) and sent into the quench vessel with 50% agitation. Next, the quench vessel was heated to 90-95° C. The contents of the tetraacid-tetra sodium salt vessel (350 kg) were then transferred into the quench vessel over 90 minutes. Next, the vessel was rinsed with DI water (35 kg) and the rinse was likewise sent to the quench vessel (580 kg total mass at 90-95° C.). Agitation of the white slurry was then gradually increased to 80% power. After a total quench time of two hours, the quench vessel was cooled to 80-85° C. At this point, a sample was found to be a non-tacky free-flowing white slurry. The solids settled quickly from the aqueous media.

A Teflon-lined flexible hose and fittings with the appropriate compatible material of construction were used to transfer the slurry from the quench vessel to an unheated 40-liter Nutsche filter, containing a 60 micron Teflon filter media filter media. Under 50 psig, the liquid was separated from the solids in the Nutsche filter and the filtrate was sent into a polypropylene tote. After the filtration was completed, the transfer process was repeated until the product cake filled the bottom section of the Nutsche filter. The filter was then depressurized.

A hold tank was filled with DI water, heated to 90° C., and pressurized to 50 psig. Water was then transferred from the hold tank to the Nutsche filter, and then the system was closed and allowed to soak for 30 minutes. The Nutsche filter was then pressurized to remove the water. This batch-flushing protocol was repeated several times. As before, the filtrate was sent into a polypropylene tote. The waste stream was monitored until a pH of 2.9 or higher was obtained. The water flow was then halted, the filter was pressurized to 50 psig to remove most of the water, and the wet cake was finally transferred into a plastic drum. This cake isolation procedure was continued until all BPoTA was collected. The pan solids analysis of cake indicated average wt % solids in the range of 85%. A total of 43.21 kg of the white BPoTA wet cake was isolated with an estimated dry mass of 36.72 kg. The combined wet cakes were used directly in the ring-closure step without further drying. ICP-Dig: sodium (184), potassium (15 ppm), zinc (1 ppm), calcium (8 ppm), aluminum (9 ppm), iron (6 ppm), titanium (0 ppm), phosphorus (9 ppm), chromium (5 ppm); IC-Total: sulfates (1219 ppm), phosphates (<20 ppm), chlorides (1413 ppm), fluorides (<20 ppm); IC-Extract: sulfates (54.3 ppm), phosphates (<<0.5 ppm), chlorides (1.7 ppm), fluorides (<0.5 ppm).

The combined BPoTA wet cakes (36.72 kg dry basis, 71.42 mol) and o-DCB (200 kg) was charged into the vessel to make 15 wt % mixture. Nitrogen was applied, the mixture was agitated, and then the contents were heated to 180-185° C. and maintained at this temperature for 3-4 hours. The Karl-Fisher analysis of an overhead sample showed moisture content of 21 ppm. Then, the UPLC analysis on the reactor sample indicated that cyclization to BPoDA was complete. The reactor content was then was diluted to 5-7 wt % solids (total reactor mass of 625 kg) by adding hot o-DCB from another vessel. The 2 micron Mott filter was heated to 175-180° C. while maintaining the vessel temperature 180-185° C. for 2 h with 50% agitation. The contents were subsequently sent through the Mott filter and into the cleaned vessel to remove any residual inorganic species present. The filtrate was concentrated to 225 kg (16-17 wt % solids) and then cooled down to 70-75° C. with increased agitation. A visual inspection of the reactor sample helped to confirm that crystallization had occurred and formed a light beige-colored precipitate having good flow with no tackiness. The solids settled quickly from the cooled o-DCB media.

Next, filtration of the BPoDA/o-DCB slurry was performed using Nutsche filter to collect 3,3'-BPoDA product. A Teflon-lined flexible hose and fittings with the appropriate compatible material of construction was used to transfer the slurry from crystallization vessel to an unheated 40 liter Nutsche filter, containing a Teflon® filter media. Under 50 psig, the liquid was separated from the solids in the Nutsche filter and the filtrate was sent into a carbon steel drum. The filtration of slurry continued until the sufficient cake build up was observed. The filter was then pressurized to 50 psig to remove most of the o-DCB. The filter was then depressurized to remove the product. The isolation process was repeated until all the product solids were collected. A total of 28.30 kg of the light-beige colored DA powder was isolated with after drying at 140-145° C. (30 inches Hg) for 48 hours. UPLC: 3,3'-BPoDA and isomers (98.40%), an unknown peak (1.6%); ICP-Dig: sodium (0 ppm), potassium (0.5 ppm), zinc (0 ppm), calcium (4.6 ppm), aluminum (11.5 ppm), iron (15 ppm), titanium (0 ppm), phosphorus (13.6 ppm); IC-Extract: sulfates (10.2 ppm), phosphates (<0.5 ppm), nitrates (<0.5 ppm), nitrites (<0.5 ppm), chlorides (<0.5 ppm), fluorides (0.8 ppm).

Example 10

To a solution of N,N'-Ph-BPoBI (a mixture of N,N'-Ph-3,3'-BPoBI, N,N'-3,4'-BPoBI, N,N'-4,4'-BPoBI isomers) in o-DCB (210 kg at 21-23 wt % solids) was added DI water (275 kg). The reactor was agitated at 90% power with a nitrogen purge. A solution of 50% aqueous NaOH (45.98 kg, 575.20 mol, 6.0 equiv.) was then added hydrolysis vessel. The contents (600 kg) were then sealed with the nitrogen regulator set to 10 psig and heated over the next three hours until the internal pressure reached 130-135 psig (180° C.). The pressure was maintained at 130-135 psig for an additional 4-5 hours with agitation. The contents were cooled to 85-90° C. and the vessel was carefully depressurized to 2 psig after which a sample was taken for stoichiometry determination. UPLC analyses of the reaction mixture showed that hydrolysis was complete.

Agitation was ceased and the layers were allowed to separate over 60 minutes while maintaining an internal temperature of 90-95° C. The bottom (o-DCB/aniline/small amount of precipitated BPoTA•4Na) layer was sent through the filter to collect precipitated product. Then, another 170 kg of hot DI water was added to help phase separate. The bottom layer sent through a filter was discarded to waste. At this point the reaction vessel contained a top layer comprising $H_2O$, aniline and BPoTA•4Na at approximately 10 wt % solids. The top layer containing product in water was heated to 120-125° C. with 50% agitation.

A hold tank was charged with DI water, which was then heated to 95° C. and sent to the hydrolysis vessel as needed to maintain 350 kg weight (16 wt % solids) in the reactor as the azeotrope distilled out at 120-125° C. Overheads were monitored every 30 minutes for the presence of aniline. Agitation was reduced to 20% power and the tempered oil was reduced to 120° C. Removal of the aniline byproduct was monitored using UPLC analysis of the reactor sample. The weight of the vessel was maintained 350 kg. Next, the solution was maintained at 90° C. with agitation.

A quench vessel was charged with DI water (100 kg), agitated without heat, and then charged with 50% aqueous $H_2SO_4$ (62.05 kg, 316.3 mol, 3.3 equiv.) via a Teflon-lined drum pump with a PVC flexible hose. The transfer lines were subsequently flushed with DI water (20 kg) and sent into the quench vessel with 50% agitation. Next, the quench vessel was heated to 90-95° C. The contents of the tetraacid-tetra sodium salt vessel were then transferred into the quench vessel over 90 minutes. Next, the vessel was rinsed with DI water (35 kg) and the rinse was likewise sent to the quench vessel (605 kg total mass at 90-95° C.). Agitation of the white slurry was then gradually increased to 80% power. After a total quench time of two hours, the quench vessel was cooled to 70-80° C. At this point, a sample was found to be a non-tacky free-flowing white slurry. The solids settled quickly from the aqueous media.

A Teflon-lined flexible hose and fittings with the appropriate compatible material of construction were used to transfer the slurry from the quench vessel to an unheated 40-liter Nutsche filter, containing a 60 micrometer Teflon filter media filter media. Under 50 psig, the liquid was separated from the solids in the Nutsche filter and the filtrate was sent into a polypropylene tote. After the filtration was completed, the transfer process was repeated until the product cake filled the bottom section of the Nutsche filter. The filter was then depressurized.

A hold tank was filled with DI water, heated to 90° C., and pressurized to 50 psig. Water was then transferred from the hold tank to the Nutsche filter, and then the system was closed and allowed to soak for 30 minutes. The Nutsche filter was then pressurized to remove the water. This batch-flushing protocol was repeated several times. As before, the filtrate was sent into a polypropylene tote. The waste stream was monitored until a pH of 2.9 or higher was obtained. The water flow was then halted, the filter was pressurized to 50 psig to remove most of the water, and the wet cake was finally transferred into a plastic drum. This cake isolation procedure was continued until all BPoTA was collected. The pan solids analysis of cake indicated wt % solids in the range of 88-92%. A total of 48.41 kg of the white BPoTA wet cake was isolated with an estimated dry mass of 43.10 kg. The combined wet cakes were used directly in the ring-closure step without further drying. ICP-Dig: sodium (138), potassium (9 ppm), zinc (2 ppm), calcium (6 ppm), aluminum (2 ppm), iron (20 ppm), titanium (0 ppm), phosphorus (7 ppm), chromium (10 ppm), magnesium (19 ppm), nickel (2 ppm); IC-Total: sulfates (301 ppm), phosphates (<20 ppm), chlorides (919 ppm); IC-Extract: sulfates (278 ppm), phosphates (2.4 ppm), chlorides (1.2 ppm), fluorides (3.0 ppm), bromide (<0.5 ppm), nitrate (<0.5 ppm), nitrite (<0.5 ppm).

The combined BPoTA wet cakes (48.41 kg we basis, wt % solids=88-92%) and o-DCB (200 kg) was charged into the vessel. Nitrogen was applied, the mixture was agitated, and then the contents were heated to 180-185° C. and maintained at this temperature for 4-5 hours. The Karl-Fisher analysis of an overhead sample showed moisture content of 16 ppm. Then, a reactor sample was taken, and UPLC analysis on the reactor sample indicated that reaction was complete (no BPoTA peak was seen). The reaction content was maintained at 145-150° C. for overnight. The temperature was then increased to 180° C. and the reactor content was then was diluted to 7.5 wt % solids (total reactor mass of 682 kg) by adding hot o-DCB from another vessel. The 2 micron Mott filter was heated to 175-180° C. while maintaining the vessel temperature 180-185° C. for 2 h with 50% agitation. The contents were subsequently sent through the Mott filter and into the cleaned vessel to remove any residual inorganic species present. The filtrate was concentrated to 250 kg (16-17 wt % solids) and then cooled down to 70-75° C. with increased agitation. A visual inspection of the reactor sample helped to confirm that crystallization had occurred and formed a light beige-colored precipitate having good flow with no tackiness. The solids settled quickly from the cooled o-DCB media.

Next, filtration of the BPoDA/o-DCB slurry was performed using Nutsche filter to collect 3,3'-BPoDA product. A Teflon-lined flexible hose and fittings with the appropriate compatible material of construction was used to transfer the slurry from crystallization vessel to an unheated 40 liter Nutsche filter, containing a Teflon® filter media. Under 50 psig, the liquid was separated from the solids in the Nutsche filter and the filtrate was sent into a carbon steel drum. The filtration of slurry continued until the sufficient cake build up was observed. The filter was then pressurized to 50 psig to remove most of the o-DCB. The filter was then depressurized to remove the product. The isolation process was repeated until all the product solids were collected. A total of 33.60 kg of the light-beige colored DA powder was isolated with after drying at 140-145° C. (30 inches Hg) for 48 hours. UPLC: 3,3'-BPoDA, isomers and diacid anhydride (99.34%), an unknown peak (0.66%); ICP-Dig: sodium (7 ppm), potassium (22 ppm), zinc (2 ppm), calcium (6 ppm), aluminum (4 ppm), iron (15 ppm), titanium (1 ppm), phosphorus (11 ppm), nickel (2 ppm), magnesium (0 ppm), copper (0 ppm), chromium (2 ppm); IC-Extract: sulfates (8.2 ppm), phosphates (<0.5 ppm), nitrates (<0.5 ppm), nitrites (<0.5 ppm), chlorides (<0.5 ppm), fluorides (0.8 ppm), bromides (<0.5 ppm).

Example 11

The following procedure used 3,3'-BPoTA which had the following profile: ICP-Dig: sodium (10 ppm), potassium (15 ppm), zinc (0 ppm), calcium (5 ppm), aluminum (0 ppm), iron (4 ppm), titanium (0 ppm), phosphorus (9 ppm); IC-Total: sulfates (<20 ppm), chloride (316 ppm).

The combined BPoTA wet cakes (87 kg wet basis, 85-86 wt % solids) and o-DCB (250 kg) was charged into the vessel. Nitrogen was applied, the mixture was agitated, and then the contents were heated to 180-185° C. and maintained at this temperature for 4-5 hours (19-20 wt % solids). The Karl-Fisher analysis of an overhead sample showed moisture content of 41 ppm. Then, a reactor sample was taken, and UPLC analysis on the reactor sample indicated that reaction was complete (no BPoTA peak was seen). The reaction content was maintained at 145-150° C. for overnight. The temperature was then increased to 180° C. and the reactor content was then was diluted to 7.5 wt % solids (total reactor mass of 810 kg) by adding hot o-DCB from another vessel. The 2 micrometer Mott filter was heated to 175-180° C. while maintaining the vessel temperature 180-185° C. for 2 h with 50% agitation. The contents were subsequently sent through the Mott filter and into the cleaned vessel to remove any residual inorganic species present. The filtrate was concentrated to 360 kg (16-17 wt % solids) and then cooled down to less than 60° C. with increased agitation. A visual inspection of the reactor sample helped to confirm that crystallization had occurred and formed a light beige-colored precipitate having good flow with no tackiness. The solids settled quickly from the cooled o-DCB media.

Next, filtration of the BPoDA/o-DCB slurry was performed using centrifuge to collect 3,3'-BPoDA product. A Teflon-lined flexible hose and fittings with the appropriate compatible material of construction was used to transfer the slurry from crystallization vessel to an unheated centrifuge. The centrifuge was spun using 100 rpm to separate liquid from the solids and the filtrate was sent into a carbon steel drum. The filtration of slurry continued until the sufficient cake build up was observed. The centrifuge was spun for 2 hours to ensure removal of most of the o-DCB. The cake was then discharged from the centrifuge. The isolation process was repeated until all the product was collected. A total of 51.60 kg of the light-beige colored DA powder was isolated after drying at 140-145° C. (30 inches Hg) for 48 hours. UPLC: 3,3'-BPoDA, isomers and diacid anhydride (99.34%), an unknown peak (0.66%); ICP-Dig: sodium (2 ppm), potassium (5 ppm), zinc (0 ppm), calcium (0 ppm), aluminum (0 ppm), iron (0 ppm), titanium (0 ppm), phosphorus (12 ppm), nickel (0 ppm), magnesium (0 ppm), copper (0 ppm), chromium (0 ppm); IC-Extract: sulfates (10.1 ppm), phosphates (<0.5 ppm), nitrates (<0.5 ppm), nitrites (<0.5 ppm), chlorides (<0.5 ppm), fluorides (0.8 ppm), bromides (<0.5 ppm).

Comparative Example 12

To a 250 mL 3-neck round-bottom flask with mechanical stirrer, Dean-Stark trap and condenser, 3,3'-BPoTA (30 g, 58.31 mmol), acetic acid (55 g, 52 mL) and acetic anhydride (55 g, 51 mL) were added. The flask was then placed in an oil bath and heated to 130° C. under nitrogen. After 5-6 hours, UPLC analysis indicated the reaction was complete and a light gray colored precipitate in solvent mixture was observed. The mixture was then cooled to room temperature. The product was collected by filtration and then washed with hot DI water (2×35 mL). The product was allowed to dry in the vacuum oven at 140-145° C. until a consistent mass was obtained. In this manner, 22.60 g (81% yield) of the 3,3'-BPoDA product was collected. UPLC: BPoDA isomers (97.8%); ICP-Dig: sodium (5 ppm), potassium (12 ppm), zinc (1 ppm), calcium (13 ppm), aluminum (4 ppm), iron (11 ppm), titanium (0 ppm), phosphorus (6 ppm); IC-Extract: sulfates (21.0 ppm), chloride (<0.5 ppm), phosphates (1.6 ppm), nitrates (<0.5 ppm), nitrites (<0.5 ppm).

A variety of conditions were used to determine which were most effective in the purification of BPoDA from organic and inorganic contaminants. The results are summarized in Table 2. The results showed that the cyclization of BPoTA to BPoDA can be achieved in a chlorinated solvent such as o-DCB in the presence or the absence of a promoter. The BPoDA showed limited solubility in the chlorinated solvent at the boiling point temperature under standard atmospheric pressure conditions. For example, the BPoDA showed less than 15 wt % solubility in o-DCB at 180-185° C. Different purification conditions were employed, which involved crystallization followed by washing, Mott filtration of the homogenous solution followed by crystallization, and slurry-liquid extraction with sodium bicarbonate. The results showed that crystallization followed by washing of the isolated solids (example 1 and comparative example 2) helped to remove sulfate contaminants, but did not impact the sodium levels. Additional washing of crystallized dianhydride material with water (comparative example 3) failed to significantly remove excess sodium. However, simple crystallization of the dianhydride followed by water washing of the solids (examples 4-7) did provide the BPoDA product with sodium content lower than 25 ppm when the tetraacid starting material contained less than 100 ppm sodium. Interestingly, slurry-liquid extraction with sodium bicarbonate (example 8) provided BPoDA product with sulfates lower than 25 ppm but sodium levels greater than 110 ppm. Finally, Mott filtration of the homogenous dianhydride solutions followed by crystallization (examples 9-11) removed both sodium and sulfate impurities to very low levels (<11 ppm).

TABLE 2

| | BPoTA | | BPoDA | | |
|---|---|---|---|---|---|
| Example | Sodium (initial) | Sulfate (initial) | Purification Conditions | Sodium (final) | Sulfate (final) |
| 1 | 25 | 81.3 | Crystallization + Washing | 24.5 | <1.0 |
| 2* | 139 | 75.1 | Crystallization + Washing | 147 | 8.2 |
| 3* | 147 | 8.2 | Crystallization + DI Water Washing | 114 | 9.1 |
| 4 | 52 | — | Crystallization + Washing | 23.5 | — |
| 5 | 92 | — | Crystallization + Washing | 21.6 | — |
| 6 | 89 | — | Crystallization + Washing | 16 | — |
| 7 | 79 | — | Crystallization + Washing | 22 | — |

TABLE 2-continued

| | BPoTA | | BPoDA | | |
|---|---|---|---|---|---|
| Example | Sodium (initial) | Sulfate (initial) | Purification Conditions | Sodium (final) | Sulfate (final) |
| 8 | 220 | 201.8 | Slurry-Liquid Extraction | 200 | 15.5 |
| 9 | 184 | 54.3 | Mott Filtration + Crystallization | 0 | 10.2 |
| 10 | 138 | 278 | Mott Filtration + Crystallization | 7 | 8.2 |
| 11 | 10 | <20 | Mott Filtration + Crystallization | 2 | 10.1 |
| 12* | 138 | 278 | crystallization | 5 | 21 |

*denotes Comparative Examples

Example 13

The following procedure used 3,3'-BPoDA which had the following profile: ICP-Dig: sodium (24.5 ppm), potassium (3.6 ppm), aluminum (2.1 ppm), iron (3.6 ppm), titanium (2.4 ppm), phosphorus (5.2 ppm); IC-Extract: sulfates (1.01 ppm), chlorides (<0.5 ppm), phosphates (<0.5 ppm), nitrates (<0.5 ppm), nitrites (<0.5 ppm).

To a reactor vessel under nitrogen with a mechanical stirrer, condenser, and solvent recirculation loop was charged 3,3'-BPoDA (3.2 kg, 6.69 mol), m-PD (740.44 g, 6.847 mol), PA (64.30 g, 0.425 mol), and o-DCB (7.65 L, 10.00 kg) all at once. The reactor content was mixed at 15-17 rpm without heating under a nitrogen purge for 5-10 minutes. The mixture was then heated to reflux for 30 minutes with internal temperature target of 185-195° C. It was observed that reaction passes through short clumpy phase. During the next 1-2 hours, the overheads ($H_2O$) were removed and the agitation and nitrogen flow was increased to 28-30 rpm and 0.5 scfm, respectively. Once the reaction reached targeted 25% solids, the overheads were allowed to recirculate back into the reactor, and the temperature set point was slowly adjusted up to a strong reflux over the next 2-3 hours.

After a heating and mixing for 2-3 hours, a sample was taken for stoichiometric analysis. The reaction was adjusted with either m-PD or dianhydride to achieve targeted stoichiometry and molecular weight. After a total reaction time of 7 hours, the reactor content was allowed to cool overnight under nitrogen flow with no agitation. The mixture was agitated for 5-10 min at 25-30 rpm the following morning to form uniform slurry. The material was collected into a steel bucket by opening the bottom discharge valve. Once all the material was removed, the prepolymer slurry in o-DCB was vacuum filtered onto a Buchner funnel with a Whatman #1 (240 microns) filter until dry. The Haake devolatilization of polymer wetcake was performed at 365-385° C. for 15-20 minutes. The GPC analysis indicated the weight average molecular weight of 42,456 grams per mole, number average molecular weight of 15,617 grams per mole, and PDI of 2.69. Metal Analysis: ICP-Dig: sodium (28 ppm), potassium (8 ppm), zinc (4.2 ppm), calcium (9.8 ppm), aluminum (10 ppm), iron (95 ppm), titanium (1.2 ppm), phosphorus (51 ppm); IC-Extract: fluorides (<0.5 ppm), chlorides (2.0 ppm), nitrites (<0.5 ppm), bromides (<0.5 ppm), nitrates (<0.5 ppm), sulfates (3.1 ppm); DSC Tg: 267.0° C., forming highly creasable transparent yellow film.

Example 14

The following procedure used 3,3'-BPoDA which had the following profile: ICP-Dig: sodium (2 ppm), potassium (5.5 ppm), zinc (1.1 ppm), calcium (4.1 ppm), aluminum (1.5 ppm), iron (1.3 ppm), titanium (0 ppm), phosphorus (8.7 ppm); IC-Extract: sulfates (2.76 ppm), chlorides (1.61 ppm), phosphates (<0.5 ppm), nitrates (1.22 ppm), nitrites (<0.5 ppm), fluorides (<0.5 ppm).

To a reactor vessel under nitrogen with a mechanical stirrer, condenser, and solvent recirculation loop was charged 3,3'-BPoDA (3.2 kg, 6.69 mol), m-PD (744.42 g, 6.883 mol), PA (74.17 g, 0.508 mol), and o-DCB (7.65 L, 10.00 kg) all at once. The reactor content was mixed at 15-17 rpm without heating under a nitrogen purge for 5-10 minutes. The mixture was then heated to reflux for 30 minutes with internal temperature target of 185-195° C. It was observed that reaction forms a slurry in o-DCB and with increasing temperature and progressing reaction, the reaction formed a clumpy phase where a sticky mixture was observed for a short period of time, which was then broken again into a powder, reforming a uniform slurry. During the next 1-2 hours, the overheads ($H_2O$) were removed and the agitation and nitrogen flow was increased to 28-30 rpm and 0.5 scfm, respectively. Once the reaction reached targeted 25% solids, the overheads were allowed to recirculate back into the reactor, and the temperature set point was slowly adjusted up to a strong reflux over the next 2-3 hours.

After a heating and mixing for 2-3 hours, a sample was taken for stoichiometric analysis. The reaction was adjusted with either m-PD or dianhydride to achieve targeted stoichiometry and molecular weight. After a total reaction time of 6 hours, the reactor content was allowed to cool overnight under nitrogen flow with no agitation. The mixture was agitated for 5-10 min at 25-30 rpm the following morning to form uniform slurry. The material was collected into a steel bucket by opening the bottom discharge valve. Once all the material was removed, the prepolymer slurry in o-DCB was vacuum filtered onto a Buchner funnel with a Whatman #1 (240 microns) filter until dry. The Haake devolatilization of polymer wetcake was performed at 365-385° C. for 15-20 minutes. The GPC analysis indicated the weight average molecular weight of 31,842 grams per mole, number average molecular weight of 15,713 grams per mole, and PDI of 2.02. Metal analysis: ICP-Dig: sodium (2.2 ppm), potassium (5.6 ppm), zinc (3.8 ppm), calcium (8.3 ppm), aluminum (1.9 ppm), iron (7.2 ppm), titanium (0.05 ppm), phosphorus (11 ppm); IC-Extract: fluorides (<0.5 ppm), chlorides (1.4 ppm), nitrites (<0.5 ppm), bromides (<0.5 ppm), nitrates (<0.5 ppm), sulfates (<0.5 ppm); DSC Tg: 267.4° C., affording highly creasable transparent yellow film.

Example 15

The following procedure used 3,3'-BPoDA with the following profile: ICP-Dig: sodium (7 ppm), potassium (22 ppm), zinc (2 ppm), calcium (6 ppm), aluminum (4 ppm), iron (15 ppm), titanium (1 ppm), phosphorus (11 ppm); IC-Extract: sulfates (8.2 ppm), phosphates (<0.5 ppm), nitrates (<0.5 ppm), nitrites (<0.5 ppm), chlorides (<0.5 ppm), fluorides (0.7 ppm).

To a reactor vessel under nitrogen with a mechanical stirrer, condenser, and solvent recirculation loop was charged 3,3'-BPoDA (2.46 kg, 5.142 mol), m-PD (325.0 g, 3.00 mol), 4,4'-DDS (610 g, 2.457 mol), PA (108.67 g, 0.719 mol), and o-DCB (7.93 L, 10.36 kg) all at once. The reactor content was mixed at 12-15 rpm without heating under a nitrogen purge for 5-10 minutes. The mixture was then heated to reflux for 30 minutes with internal temperature target of 200-205° C. It was observed that reaction forms a slurry in o-DCB and with increasing temperature and progressing reaction, the reaction formed a sticky glue ball phase where a sticky mixture was observed for a short period of time, which was then broken again into a powder, reforming a uniform slurry. During the next 1-2 hours, the overheads ($H_2O$) were removed and the agitation and nitrogen flow was increased to 20-23 rpm and 0.5 scfm, respectively. Once the reaction reached targeted 25% solids, the overheads were allowed to recirculate back into the reactor, and the temperature set point was slowly adjusted up to a strong reflux over the next 3-4 hours.

After a heating and mixing for 3-4 hours, a sample was taken for stoichiometric analysis. The reaction was adjusted with either m-PD or dianhydride or phthalic anhydride to achieve targeted stoichiometry and molecular weight. After a total reaction time of 12-16 hours, the reactor content was allowed to cool overnight under nitrogen flow with no agitation. The mixture was agitated for 5-10 min at 25-30 rpm the following morning to form uniform slurry. The material was collected into a steel bucket by opening the bottom discharge valve. Once all the material was removed, the prepolymer slurry in o-DCB was vacuum filtered onto a Buchner funnel with a Whatman #1 (240 microns) filter until dry. The Haake devolatilization of polymer wetcake was performed at 365-385° C. for 15-20 minutes. The GPC analysis indicated the weight average molecular weight of 23,052 grams per mole, and PDI of 2.87. Metal analysis: ICP-Dig: sodium (8 ppm), potassium (13 ppm), zinc (2 ppm), calcium (16 ppm), aluminum (15 ppm), iron (26 ppm), titanium (2 ppm), nickel (2 ppm), magnesium (3 ppm), copper (3 ppm), chromium (4 ppm), phosphorus (16 ppm); IC-Extract: sulfates (2.3 ppm), chlorides (1.4 ppm), phosphates (3.2 ppm), nitrates (<0.5 ppm), nitrites (<0.5 ppm), bromides (<0.5 ppm); DSC Tg: 272.6° C., forming a highly creasable transparent yellow film. Examples 13 to Example 15 were injection molded into optical plaques with dimensions of 50 mm×75 mm×1 mm, using 380° C. to 400° C. for melt temperature and 150° C. to 200° C. for mold temperature. The term "percent light transmission" or "% T" refers to the ratio of transmitted light to incident light, and can be measured according to ASTM D 1003-07. These measurements can be taken on the molded articles above or on 0.2 mm thick films prepared on a hot press at 380° C. to 400° C.

Example 16

The following procedure used 3,3'-BPoDA with the following profile: ICP-Dig: sodium (7 ppm), potassium (22 ppm), zinc (2 ppm), calcium (6 ppm), aluminum (4 ppm), iron (15 ppm), titanium (1 ppm), phosphorus (11 ppm); IC-Extract: sulfates (8.2 ppm), phosphates (<0.5 ppm), nitrates (<0.5 ppm), nitrites (<0.5 ppm), chlorides (<0.5 ppm), fluorides (0.7 ppm).

To a reactor vessel under nitrogen with a mechanical stirrer, condenser, and solvent recirculation loop was charged 3,3'-BPoDA (3.0 kg, 6.28 mol), p-PD (399.60 g, 3.695 mol), 4,4'-ODA (603.48 g, 3.013 mol), PA (127.99 g, 0.864 mol), and o-DCB (6.50 L, 8.5 kg) all at once. The reactor content was mixed at 15-17 rpm without heating under a nitrogen purge for 5-10 minutes. The mixture was then heated to reflux for 30 minutes with internal temperature target of 185-195° C. It was again observed that reaction passed through the short clumpy phase as described above. During the next 1-2 hours, the overheads ($H_2O$) were removed and the agitation and nitrogen flow was increased to 21-28 rpm and 0.5 scfm, respectively. Once the reaction reached targeted 25% solids, the overheads were allowed to recirculate back into the reactor, and the temperature set point was slowly adjusted up to a strong reflux over the next 2-3 hours.

After a heating and mixing for 2-3 hours, a sample was taken for stoichiometric analysis. The reaction was adjusted with either m-PD or dianhydride or phthalic anhydride to achieve targeted stoichiometry and molecular weight. After a total reaction time of 4-5 hours, the reactor content was allowed to cool overnight under nitrogen flow with no agitation. The mixture was agitated for 5-10 min at 25-30 rpm the following morning to form uniform slurry. The material was collected into a steel bucket by opening the bottom discharge valve. Once all the material was removed, the prepolymer slurry in o-DCB was vacuum filtered onto a Buchner funnel with a Whatman #1 (240 microns) filter until dry. The Haake devolatilization of polymer wetcake was performed at 365-385° C. for 15-20 minutes. The GPC analysis indicated the weight average molecular weight of 32,313 grams per mole, and a PDI of 3.07. Metal analysis: ICP-Dig: sodium (3 ppm), potassium (21 ppm), zinc (4 ppm), calcium (8 ppm), aluminum (6 ppm), iron (9 ppm), titanium (5 ppm), phosphorus (11 ppm), chromium (3 ppm), copper (1 ppm), nickel (1 ppm); IC-Extract: sulfates (<0.5 ppm), chlorides (1.1 ppm), phosphates (1.1 ppm), nitrates (<0.5 ppm), nitrites (<0.5 ppm), bromides (<0.5 ppm), fluorides (0.6 ppm); DSC Tg: 273.8° C., affording highly creasable transparent yellow film.

Comparative Example 17

The following procedure used 3,3'-BPoTA with the following profile: ICP-Dig: sodium (185 ppm), potassium (37.5 ppm), zinc (4.38 ppm), calcium (8.61 ppm), aluminum (5.73 ppm), iron (25.2 ppm), titanium (0.55 ppm), phosphorus (11.1 ppm), nickel (3.34 ppm), chromium (15.9 ppm), magnesium (1.05 ppm); IC-Extract: fluorides (3 ppm), chlorides (1.2 ppm), nitrites (<0.5 ppm), bromides (<0.5 ppm), nitrates (1.5 ppm), sulfates (278.9 ppm), phosphates (2.4 ppm).

A 1000 mL 3-neck round-bottom flask equipped with a Dean-Stark trap, condenser, mechanical stirrer, and nitrogen inlet was charged with 3,3'-BPoTA (17.14 g, 33.32 mmol) and o-DCB (50 g, 38 mL). The flask was placed in an oil bath at 25° C., under nitrogen (15 scfh), agitated at 150 rpm, and began to heat to 180° C. After 60 minutes, 17 g of distillate (o-DCB/H$_2$O) was removed from the Dean-Stark trap, the nitrogen flow was reduced to 10 scfh, and agitation was increased to 300 rpm. The fresh o-DCB was added to the reaction flask to make up the solvent loss in the Dean-Stark trap. After a total of 7-8 hours, UPLC analysis indicated that the reaction was complete and had 3,3'-BPoDA in 95.06%, BPoDA isomers in 2.5% and unknown peak of 2.44%. The resultant BPoDA mixture was taken directly for polymerization by charging 4,4'-DDS (3.93 g, 38.82 mmol), m-PD (2.09 g, 72.093 mmol), and phthalic anhydride (PA) (0.581 g, 1863.9 mmol). The flask was continued to heat to 195-200° C., under nitrogen (15 scfh), agitated at 200 rpm.

After approximately thirty minutes, agitation was reduced to 70 rpm throughout the glue ball stage, (163-180° C.). After the glue ball stage, agitation was increased to 200 rpm. After a total of four hours, 42 g of distillate (o-DCB/H$_2$O) was removed from the Dean-Stark trap, the nitrogen flow was reduced to 10 scfh, and agitation was increased to 250 rpm. At this stage, the dough ball changed to uniform yellow slurry. The reaction flask was removed from an oil bath, diluted the reaction content with additional o-DCB (70 g), from the oil bath and was allowed to cool to ambient temperature. The solids were filtered using Whatman filter paper 4, then vacuum dried at 150° C. overnight. The GPC analysis of a devolatilized sample indicated this material had a weight average molecular weight of 21372 grams per mole. Hot-pressing provided a brittle amber colored film with a Tg of 252.8° C. and onset decomposition temperature of 321.8° C. in air. Metal analysis: ICP-Dig: sodium (109 ppm), potassium (8.18 ppm), zinc (3.25 ppm), calcium (24.6 ppm), aluminum (14.3 ppm), iron (8.30 ppm), titanium (<1 ppm), phosphorus (<1 ppm), chromium (4.76 ppm), copper (<1 ppm), nickel (<1 ppm), Manganese (<1 ppm), Magnesium (3.61 ppm); IC-Extract: sulfates (30.9 ppm), chlorides (1.0 ppm), phosphates (<0.5 ppm), nitrates (1.3 ppm), nitrites (<0.5 ppm), bromides (<0.5 ppm), fluorides (<0.5 ppm).

Example 18

The following procedure used 3,3'-BPoDA which had the following profile: ICP-Dig: sodium (20 ppm), potassium (7 ppm), zinc (0 ppm), calcium (2.6 ppm), aluminum (0 ppm), iron (3 ppm), titanium (0 ppm), phosphorus (8 ppm); IC-Extract: sulfates (4.6 ppm), chloride (<0.5 ppm), phosphates (<0.5 ppm), nitrates (<0.5 ppm), nitrites (<0.5 ppm); and m-PD which had the following profile:ICP-Dig: sodium (1 ppm), potassium (12 ppm), zinc (0 ppm), calcium (3 ppm), aluminum (3 ppm), iron (0 ppm), titanium (0 ppm), phosphorus (5 ppm); IC-Extract: sulfates (<0.5 ppm), chloride (130.7 ppm), phosphates (<0.5 ppm), nitrates (1.9 ppm), nitrites (<0.5 ppm).

In a 250 mL 3-neck round bottom flask affixed with a Dean-Stark trap, condenser, mechanical stirrer, and nitrogen inlet (2 scfh) was added 3,3'-BPoDA (20.81 g, 43.49 mmol), phthalic anhydride (0.726 g, 4.90 mmol), m-PD (2.70 g, 25.0 mmol), 4,4'-DDS (5.08 g, 20.5 mmol), and o-DCB (109 g). The flask was placed in an oil bath at 25° C. and began to heat to 200° C. oil bath with an agitation of 120 rpm.

After 35 minutes, the oil bath temperature reached 155° C. and a glue ball phase was observed during which agitation was reduced to 80-100 rpm. After an additional eight minutes, the oil bath temperature reached 173° C. and the mixture became a homogenous yellow solution. The agitation was then increased to 200 rpm.

After a total of 75 minutes of heating, the target oil bath temperature of 200° C. was achieved. At this point, 46 g of distillate was removed from the trap to provide reaction mixture at 30 wt % solids and the nitrogen sweep was reduced to 0.5 scfh. After a total of six hours and 45 minutes the polymerization became a viscous biphasic mixture. After an additional 70 minutes, the mixture was poured and scraped with a metal spatula into a foil pan and cooled to ambient temperature. A sample was devolatilized (hot block) for 20 minutes at 380-385° C. under nitrogen. GPC: weight average molecular weight=31,372; number average molecular weight=13,644, PDI=2.30; Mz/Mw=1.35; ICP-Dig: sodium (16), potassium (11 ppm), zinc (7 ppm), calcium (25 ppm), aluminum (6 ppm), iron (15 ppm), titanium (0 ppm), phosphorus (12 ppm); IC-Extract: sulfates (4.6 ppm), chlorides (1.4 ppm), phosphates (<0.5 ppm), nitrates (<0.5 ppm), nitrites (<0.5 ppm); DSC Tg: 278.5° C.

The following examples describe the preparation of poly (etherimide) in a halogenated solvent. The results are summarized in Table 3. The condensation polymerization of BPoDA with various diamines (e.g. m-PD, 4,4'-ODA/p-PD, m-PD/4,4'-DDS) was carried out in the presence of phthalic anhydride as a chain terminating agent. Under polymerization conditions, the polymers precipitated out of refluxing o-DCB to provide a biphasic mixture containing a prepolymer, which was then isolated by filtration and devolatilized at 380-385° C. for 15-20 minutes to obtain polymer products with finished end-groups. The results showed that BPoDA having less than 25 ppm of sodium and less than 25 ppm of sulfates and chlorides can be easily polymerized to build high molecular weight poly(etherimides). The resultant poly(etherimides) exhibited high glass transition temperatures (Tg) and formed transparent, creasable to highly creasable yellow colored films (examples 13-16 and 18). In comparison, the condensation polymerization of BPoDA having elevated levels of sodium and sulfates with m-PD and 4,4'-DDS (comparative example 17) under similar polymerization conditions led to a polymer product with lower molecular weight, significantly reduced Tg (−20° C.) and increased color (amber vs yellow) with high levels of inorganic contaminants. The resulting film was found to be brittle in nature and lacked the required mechanical properties. The formulation of this comparative example was identical to that of the inventive example, with the exception of BPoDA monomer quality. In the case of example 13 versus Example 14, a reduction in the sodium content from 28 ppm to 2 ppm in the final resin increased transmission between 7 to 16%, dependent on the wavelength of interest (Table 4). A similar effect is present between Example 15 and Example 17. This occurs both in visible wavelengths (red, 630 nm) and at infrared wavelengths. To achieve an infrared transparency over 80% at 1 mm, less than 10 ppm of sodium ions should be present in the monomer and final resin. The results clearly indicate that poly(etherimide) homopolymers or copolymers with improved thermal, mechanical and optical properties can be produced when BPoDA having significantly lower levels of organic and inorganic contaminants are used.

This disclosure further encompasses the following aspects.

Aspect 1: A method for the purification of a biphenol dianhydride composition comprising a biphenol dianhydride of the formula

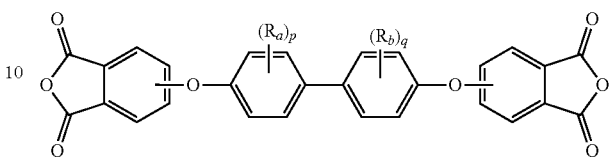

wherein $R^a$ and $R^b$ are each independently a halogen or a monovalent $C_{1-6}$ alkyl group and p and q are each independently an integer of 0 to 4, preferably wherein p and q are each 0; and at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions; the method comprising: contacting the biphenol dianhydride composition with a halogenated solvent under conditions effective to form a solution comprising the biphenol dianhydride composition; and isolating a purified biphenol dianhydride composition from the solution; wherein isolating the purified biphenol dianhydride composition from the solution comprises: cooling the solution to induce crystallization of the purified biphenol dianhydride composition to form a slurry, filtering the slurry to form a wet cake comprising the purified biphenol dianhydride composition, and washing the wet cake with water, a $C_{1-6}$ alcohol, or a combination thereof; or filtering the solution, preferably wherein the filtering is at a temperature of 160 to 225° C., preferably 160 to 190° C., more preferably 165 to 185° C., and optionally cooling the filtered solution to crystallize the purified biphenol dianhydride composition; or washing the solution with an aqueous alkaline solution, preferably wherein the aqueous alkaline solution comprises sodium bicarbonate; or adding an adsorbent to the solution to remove ionic species from the solution, and filtering the solution to remove the adsorbent and ionic species; or a combination thereof.

Aspect 2: A method of making a biphenol dianhydride composition, the method comprising: contacting a biphenol tetraacid of the formula

TABLE 3

| | BPoDA | | | Poly(etherimide) | | | | | |
|---|---|---|---|---|---|---|---|---|---|
| Ex | Sodium (initial) | Chloride (initial) | Sulfate (initial) | Mw, g/mol | Film quality | Tg (° C.) | Sodium (final) | Chloride (final) | Sulfate (final) |
| 13 | 24.5 | <0.5 | 1.0 | 42,456 | Creasable, yellow colored | 267.0 | 28 | 2.0 | 3.1 |
| 14 | 2 | 1.61 | 2.76 | 31,842 | Creasable, yellow colored | 267.4 | 2.2 | 1.4 | <0.5 |
| 15 | 7 | <0.5 | 8.2 | 23,052 | Creasable, yellow colored | 272.6 | 8 | 1.4 | 2.3 |
| 16 | 7 | <0.5 | 8.2 | 32,313 | Creasable, yellow colored | 273.8 | 3 | 1.1 | <0.5 |
| 17* | 185 | 1.2 | 278.9 | 21,372 | Brittle, amber colored | 252.8 | 109 | 1.0 | 30.9 |
| 18 | 20 | <0.5 | 4.6 | 31,372 | Creasable, yellow colored | 278.5 | 16 | 1.4 | 4.6 |

*denotes Comparative Examples

TABLE 4

| | Poly(etherimide) | | | | |
|---|---|---|---|---|---|
| Ex. | Thickness (mm) | % T (630 nm) | % T (850 nm) | % T (1310 nm) | % T (1550 nm) |
| 13 | 1 | 44.3 | 65 | 77.8 | 77.9 |
| 14 | 1 | 59.8 | 78.1 | 85.1 | 85.4 |
| 15 | 1 | 63.1 | 81.8 | 85.6 | 85.7 |
| 16 | ~0.2 | 76.7 | 87.4 | 88.9 | 88.7 |
| 17* | ~0.2 | 44.7 | 65.3 | 73.0 | 76.1 |
| 18 | ~0.2 | | | | |

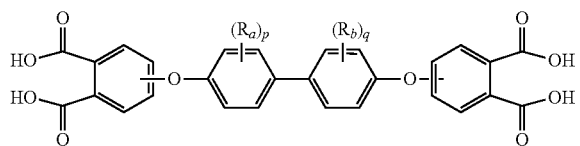

wherein $R^a$ and $R^b$ are each independently a halogen or a monovalent $C_{1-6}$ alkyl group and p and q are each independently an integer of 0 to 4, preferably wherein p and q are each 0; and at least one of sodium ions, potassium ions, calcium ions, zinc ions, aluminum ions, iron ions, nickel ions, titanium ions, chromium ions, magnesium ions, manganese ions, copper ions, phosphorus ions, phosphate ions, sulfate ions, chloride ions, bromide ions, fluoride ions, nitrate ions, and nitrite ions; with a halogenated solvent to provide a first solution; subjecting the first solution to a condition effective to form the corresponding biphenol dianhydride from the biphenol tetraacid; and isolating a purified biphenol dianhydride composition; wherein isolating the purified biphenol dianhydride composition from the solution comprises: cooling the solution to induce crystallization of the purified biphenol dianhydride composition to form a slurry, filtering the slurry to form a wet cake comprising the purified biphenol dianhydride composition, and washing the wet cake with water, a $C_{1-6}$ alcohol, or a combination thereof; or filtering the solution, preferably wherein the filtering is at a temperature of 160 to 225° C., preferably 160 to 190° C., more preferably 165 to 185° C., and optionally cooling the filtered solution to crystallize the purified biphenol dianhydride composition; or washing the solution with an aqueous alkaline solution, preferably wherein the aqueous alkaline solution comprises sodium bicarbonate; or adding an adsorbent to the solution to remove ionic species from the solution, and filtering the solution to remove the adsorbent and ionic species; or a combination thereof.

Aspect 3: The method of aspect 1 or 2, wherein isolating the purified biphenol dianhydride composition comprises cooling the solution to induce crystallization of the purified biphenol dianhydride composition to form a slurry, filtering the slurry to form a wet cake comprising the purified biphenol dianhydride composition, and the method further comprises washing the wet cake with water, a $C_{1-6}$ alcohol, or a combination thereof.

Aspect 4: The method of aspect 1 or 2, wherein isolating the purified biphenol dianhydride composition comprises filtering the solution, preferably wherein the filtering is at a temperature of 160 to 225° C., preferably 160 to 190° C., more preferably 165 to 185° C., and optionally cooling the filtered solution to crystallize the purified biphenol dianhydride composition.

Aspect 5: The method of any of aspects 1 to 3, wherein the solution has a solids content of 5 to 25 weight percent, preferably 7 to 25 weight percent, more preferably 7 to 15 weight percent.

Aspect 6: The method of any of aspects 1 to 5, wherein isolating the purified biphenol dianhydride composition comprises washing the solution with an aqueous alkaline solution, preferably wherein the aqueous alkaline solution comprises sodium bicarbonate.

Aspect 7: The method of any of aspects 1 to 6, further comprising adding an adsorbent to the solution to remove ionic species from the solution, and filtering the solution to remove the adsorbent and ionic species.

Aspect 8: The method of any of aspects 1 to 7, wherein the halogenated solvent comprises ortho-dichlorobenzene, meta-dichlorobenzene, para-dichlorobenzene, chlorobenzene, 1,2,3-trichlorobenzene, 1,3,5-trichlorobenzene, 1,2,4-trichlorobenzene, bromobenzene, 1,2,4,5-tetrachlorobenzene, 1,2,3,4-tetrachlorobenzene, 1,2,3,5-tetrachlorobenzene, 2-chlorophenol, 4-chlorophenyl phenyl ether, m-chlorotoluene, o-chlorotoluene, p-chlorotoluene or a combination thereof.

Aspect 9: The method of any of aspects 1 to 8, wherein the biphenol dianhydride is an isomer mixture, preferably wherein 2-100 weight percent of the biphenol dianhydride have the divalent bonds of the biphenol group of the biphenol dianhydride are in the 3,3' position, more preferably wherein 90-100 weight percent of the biphenol dianhydride have the divalent bonds of the biphenol group of the biphenol dianhydride are in the 3,3' position.

Aspect 10: A biphenol dianhydride made by the method of any of aspects 1 to 9, wherein the purified biphenol dianhydride comprises less than 25 ppm each of sodium ions, potassium ions, calcium ions, zinc ions, aluminum ions, nickel ions, titanium ions, chromium ions, magnesium ions, manganese ions, copper ions, phosphorus ions, and iron ions; less than 175 ppm total of sodium ions, potassium ions, calcium ions, zinc ions, aluminum ions, nickel ions, titanium ions, chromium ions, magnesium ions, manganese ions, copper ions, phosphorus ions, and iron ions; less than 35 ppm each of phosphate ions, sulfate ions, chloride ions, bromide ions, fluoride ions, nitrate ions, and nitrite ions; and less than 50 ppm total of phosphate ions, sulfate ions, chloride ions, bromide ions, fluoride ions, nitrate ions, and nitrite ions.

Aspect 11: A poly(etherimide) comprising repeating units derived from polymerization of the purified biphenol dianhydride composition made by the method of any of aspects 1 to 10 and an organic diamine.

Aspect 12: The poly(etherimide) of aspect 11, wherein the organic diamine is 4,4'-diaminodiphenylsulfone, 3,4'-diaminodiphenylsulfone, 3,3'-diaminodiphenylsulfone, meta-phenylene diamine, para-phenylene diamine, ortho-phenylene diamine, 4,4'-oxydianiline, 3,4'-oxydianiline, 3,3'-oxydianiline or a combination thereof.

Aspect 13: The poly(etherimide) of aspects 11 or 12, wherein the poly(etherimide) comprises less than 25 ppm each of sodium ions, potassium ions, calcium ions, zinc ions, aluminum ions, and iron ions, nickel ions, chromium ions, magnesium ions, manganese ions, titanium ions, copper ions, phosphorus ions, and less than 35 ppm each of phosphate ions, sulfate ions, chloride ions, nitrate ions, bromide ions, fluorides ions, and nitrite ions.

Aspect 14: The poly(etherimide) of aspects 11 to 13, wherein an article molded from the poly(etherimide) or a pressed film comprising the poly(etherimide) has a percent transmission that is greater than 40% at 630 nanometers, 850 nanometers, 1310 nanometers, and 1550 nanometers, measured according to ASTM D 1003-07.

Aspect 15: An article comprising the poly(etherimide) of any one of aspects 11 to 14, preferably wherein the article is an optical component.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. The term "combination thereof" as used herein includes one or more of the listed elements, and is open, allowing the presence of one or more like elements not named. In addition, it is to be understood that the described elements may be combined in any suitable manner in the various embodiments.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (—CN), a C$_{1-6}$ alkyl sulfonyl (—S(=O)$_2$-alkyl), a C$_{6-12}$ aryl sulfonyl (—S(=O)$_2$-aryl), a thiol (—SH), a thiocyano (—SCN), a tosyl (CH$_3$C$_6$H$_4$SO$_2$—), a C$_{3-12}$ cycloalkyl, a C$_{2-12}$ alkenyl, a C$_{5-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example —CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for the purification of a biphenol dianhydride composition comprising
   a biphenol dianhydride of the formula

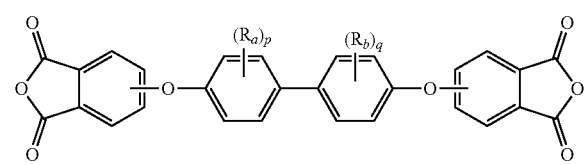

wherein R$^a$ and R$^b$ are each independently a halogen or a monovalent C$_{1-6}$ alkyl group and p and q are each independently an integer of 0 to 4; and
   at least one of sodium ions, potassium ions, calcium ions, aluminum ions, magnesium ions, phosphate ions, sulfate ions, or chloride ions, bromide ions, or nitrate ions;
   the method comprising:
   contacting the biphenol dianhydride composition with a halogenated aromatic solvent under conditions effective to form a solution, the conditions including heating the solution in a range from 150° C. to 250° C. with stirring; and isolating a purified biphenol dianhydride composition from the solution, wherein the isolating the purified biphenol dianhydride comprises:
i. cooling the heated solution to less than 100° C. to induce crystallization to form a slurry,
  filtering the slurry to form a wet cake comprising the purified biphenol dianhydride composition, and washing the wet cake with water, a $C_{1-6}$ alcohol, or a combination thereof; or
ii. filtering the heated solution followed by process i; or
iii. washing the solution with an aqueous alkaline solution at a temperature of 50° C. to less than 100 C followed by separation of solids; or
iv. adding an adsorbent to the solution to remove ionic species from the solution, and filtering the solution to remove the adsorbent and ionic species; or
a combination thereof,
with the proviso that the method does not include conversion back to a tetracarboxylic acid form of the biphenol dianhydride.

2. The method of claim 1, wherein the isolating the purified biphenol dianhydride composition further comprises washing the wet cake with water, a $C_{1-6}$ alcohol, or a combination thereof.

3. The method of claim 1, wherein the contacting of the biphenol dianhydride composition with the halogenated aromatic solvent provides for a solids content of 5 to 25 weight percent.

4. The method of claim 1, wherein the isolating the purified biphenol dianhydride composition comprises the washing of the solution with the aqueous alkaline solution.

5. The method of claim 1, wherein the isolating the purified biphenol dianhydride composition comprises the adding of the adsorbent to the solution.

6. The method of claim 1, wherein the halogenated aromatic solvent comprises ortho-dichlorobenzene, meto-dichlorobenzene, para-dichlorobenzene, chlorobenzene, 1,3,5-trichlorobenzene, 1,2,3-trichlorobenzene, 1,2,4-trichlorobenzene, 1,2,4,5-tetrachlorobenzene, 1,2,3,4-tetrachlorobenzene, 1,2,3,5-tetrachlorobenzene, bromobenzene, 2-chlorophenol, 4-chlorophenyl phenyl ether, m-chlorotoluene, o-chlorotoluene, p-chlorotoluene or a combination thereof.

7. The method of claim 1, wherein the biphenol dianhydride is mixture of isomers.

8. The method of claim 1, wherein the purified biphenol dianhydride comprises
less than 25 ppm each of sodium ions, potassium ions, calcium ions, and magnesium ions; and
less than 50 ppm total of phosphate ions, sulfate ions, chloride ions, bromide ions, and nitrate ions.

9. A method for the purification of a biphenol dianhydride composition comprising
a biphenol dianhydride of the formula

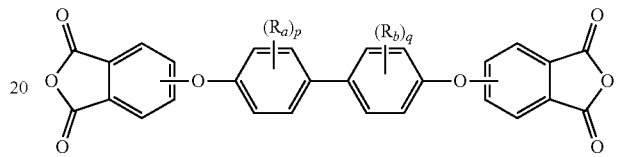

wherein $R^a$ and $R^b$ are each independently a halogen or a monovalent $C_{1-6}$ alkyl group and p and q are each independently an integer of 0 to 4; and
at least one of sodium ions, potassium ions, magnesium ions aluminum ions, phosphate ions, sulfate ions, chloride ions, bromide ions, fluoride ions, and nitrate ions;
the method comprising:
contacting the biphenol dianhydride composition with a halogenated aromatic solvent under conditions effective to form a solution; and
isolating a purified biphenol dianhydride composition from the solution, wherein the isolating the purified biphenol dianhydride comprises washing the solution with an aqueous alkaline solution.

10. The method of claim 9, wherein the washing of the solution is conducted at a temperature of 50° C. to less than 100 C with separation of an organic phase and cooling of the organic phase to form the purified biphenol dianhydride.

* * * * *